US011124543B2

(12) United States Patent
Berger et al.

(10) Patent No.: US 11,124,543 B2
(45) Date of Patent: Sep. 21, 2021

(54) SELF-ASSEMBLED STRUCTURES COMPOSED OF MONOMERS OF PEPTIDE NUCLEIC ACID AND TUNABLE PHOTONIC CRYSTALS MADE THEREFROM

(71) Applicant: Ramot at Tel-Aviv University Ltd., Tel-Aviv (IL)

(72) Inventors: Or Berger, Tiberias (IL); Lihi Adler-Abramovich, Herzlia (IL); Ehud Gazit, Ramat-HaSharon (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 454 days.

(21) Appl. No.: 15/769,082

(22) PCT Filed: Oct. 19, 2016

(86) PCT No.: PCT/IL2016/051134
§ 371 (c)(1),
(2) Date: Apr. 18, 2018

(87) PCT Pub. No.: WO2017/068584
PCT Pub. Date: Apr. 27, 2017

(65) Prior Publication Data
US 2018/0298062 A1    Oct. 18, 2018

Related U.S. Application Data

(60) Provisional application No. 62/243,192, filed on Oct. 19, 2015.

(51) Int. Cl.
| | |
|---|---|
| *C07K 14/00* | (2006.01) |
| *B82Y 20/00* | (2011.01) |
| *B82Y 40/00* | (2011.01) |
| *G01N 21/65* | (2006.01) |
| *C09K 11/06* | (2006.01) |

(52) U.S. Cl.
CPC ............ *C07K 14/003* (2013.01); *B82Y 20/00* (2013.01); *B82Y 40/00* (2013.01); *C09K 11/06* (2013.01); *G01N 21/658* (2013.01); *C09K 2211/1441* (2013.01)

(58) Field of Classification Search
CPC .............................. C07K 14/003; B82Y 20/00
See application file for complete search history.

(56) References Cited

U.S. PATENT DOCUMENTS

| 8,309,514 | B2 | 11/2012 | Zhao et al. | |
| 9,741,948 | B2 * | 8/2017 | Berger | C07K 14/003 |
| 10,446,768 | B2 * | 10/2019 | Berger | C09K 11/06 |

FOREIGN PATENT DOCUMENTS

| WO | WO 2014/178057 | 11/2014 |
| WO | WO 2017/068584 | 4/2017 |

OTHER PUBLICATIONS

International Preliminary Report on Patentability dated May 3, 2018 From the International Bureau of WIPO Re. Application No. PCT/IL2016/051134. (8 Pages).
International Search Report and the Written Opinion dated Dec. 28, 2016 From the International Searching Authority Re. Application No. PCT/IL2016/051134. (12 Pages).
Achim et al. "Peptide Nucleic Acids", Wiley Encyclopedia of Chemical Biology, p. 1-10, 2008.
Adler-Abramovich et al. "Phenylalanine Assembly Into Toxic Fibrils Suggests Amyloid Etiology in Phenylketonuria", Nature Chemical Biology, XP002678189, 8(8): 701-706, Published Online Jun. 17, 2012.
Berger et al. "Light-Emitting Self-Assembled Peptide Nucleic Acids Exhibit Both Stacking Interactions and Watson-Crick Base Pairing", Nature Nanotechnology, 10(4): 353-360, Published Online Mar. 16, 2015.
Bonifazi et al. "Peptide Nucleic Acids in Materials Science", Artificial DNA: PNA & XNA, 3(3): 112-122, Jul.-Dec. 2012.
Davis et al. "Supramolecular Architectures Generated by Self-Assembly of Guanosine Derivatives", Chemical Society Reviews, 36(2): 296-313, Published Online Nov. 7, 2006.
England et al. "Bioinspired Micrograting Arrays Mimicking the Reverse Color Diffraction Elements Evolved by the Butterfly Pierella Luna", Proc. Natl. Acad. Sci. USA, PNAS, 111(44): 15630-15634, Nov. 4, 2014.
Fichman et al. "Self-Assembly of Short Peptides to Form Hydrogels: Design of Building Blocks, Physical Properties and Technological Applications", Acta Biomaterialia, 10(4): 1671-1682, Available Online Aug. 16, 2013.
Fleming et al. "Aromatic Peptide Amphiphiles: Significance of the Fmoc Moiety", Chemical Communications, 49(90): 10587-10589, Nov. 21, 2013.
Gur et al. "Guanine-Based Photonic Crystals in Fish Scales Form From an Amorphous Precursor", Angewandte Chemie, 125(1): 406-409, Jan. 2013.
Gur et al. "The Mechanism of Color Change in the Neon Tetra Fish: A Light-Induced Tunable Photonic Crystal Array", Angewandte Chemie, International Edition, 54(42): 12426-12430, Published Online Apr. 27, 2015.
Gur et al. "The Structural Basis for Enhanced Silver Reflectance in Koi Fish Scale and Skin", Journal of the American Chemical Society, JACS, 136(49): 17236-17242, Nov. 13, 2014.
Herring "Bioluminescent Signals and the Role of Reflectors", Journal of Optics A: Pure and Applied Optics, 2(6): R29-R38, Jun. 1, 2000.

(Continued)

*Primary Examiner* — Jezia Riley

(57) ABSTRACT

Ordered structures composed of a plurality of self-assembled peptide nucleic acid (PNA) monomers, and processes of generating same are provided. The plurality of PNA monomers includes modified PNA monomers which are N-protected PNA monomers and/or which feature at least one aromatic moiety attached to a backbone, a nucleobase and/or a nucleobase linkage unit of the PNA monomer. Tunable photonic crystals formed of the provided ordered structures, uses thereof and articles-of-manufacturing containing same are also provided.

21 Claims, 4 Drawing Sheets
(3 of 4 Drawing Sheet(s) Filed in Color)

(56) References Cited

OTHER PUBLICATIONS

Kolle et al. "Bio-Inspired Band-Gap Tunable Elastic Optical Multilayer Fibers", Advanced Materials, 25(15): 2239-2245, Published Online Jan. 27, 2013.

Levy-Lior et al. "Biogenic Guanine Crystals From the Skin of Fish May Be Designed to Enhance Light Reflectance", Crystal Growth & Design, 8(2): 507-511, Published on Web Jan. 5, 2008.

Levy-Lior et al. "Guanine-Based Biogenic Photonic-Crystal Arrays in Fish and Spiders", Advanced Functional Materials, 20(2): 320-329, Jan. 22, 2010.

Li et al. "A Highly Conspicuous Mineralized Composite Photonic Architecture in the Translucent Shell of the Blue-Rayed Limpet", Nature Communications, 6(7322): 1-11, Feb. 26, 2015.

Potyrailo et al. "Towards Outperforming Conventional Sensor Arrays With Fabricated Individual Photonic Vapour Sensors Inspired by Morpho Butterflies", Nature Communications, 6(7959): 1-12, Sep. 1, 2015.

Teyssier et al. "Photonic Crystals Cause Active Colour Change in Chameleons", Nature Communications, 6(6368): 1-7, Mar. 2, 2015.

Vukusic "Natural Photonics", Physics World, 17(2): 35-39, Feb. 2004.

Vukusic et al. "Photonic Structures in Biology", Nature, 424(6950): 852-855, Aug. 14, 2003.

Xiao et al. "Bio-Inspired Structural Colors Produced Via Self-Assembly of Synthetic Melanin Nanoparticles", ACS Nano, 9(5): 5454-5460, Published Online May 4, 2015.

Xiao et al. "Nanostructural Basis of Rainbow-Like Iridescence in Common Bronzewing Phaps Chalcoptera Feathers", Optics Express, 22(12): 14625-14636, Jun. 6, 2014.

Zhao et al. "Bio-Inspired Variable Structural Color Materials", Chemical Society Reviews, 41(8): 3297-3317, Published Online Feb. 3, 2012.

\* cited by examiner

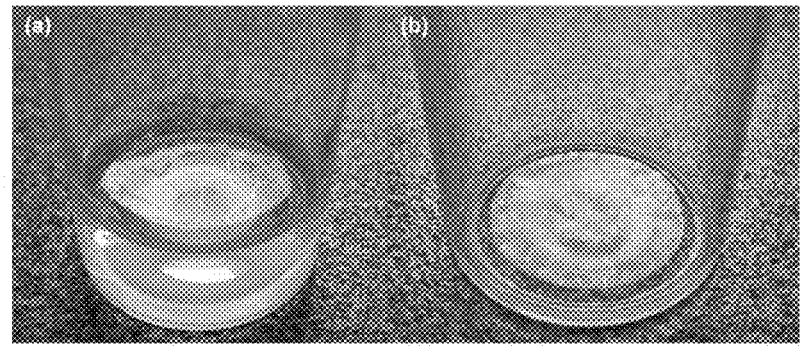
FIG. 2A FIG. 2B
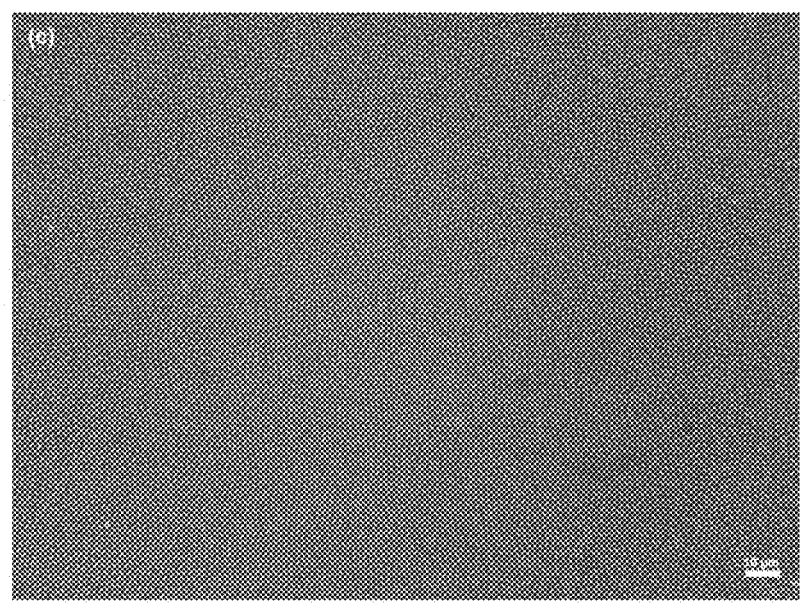
FIG. 2C
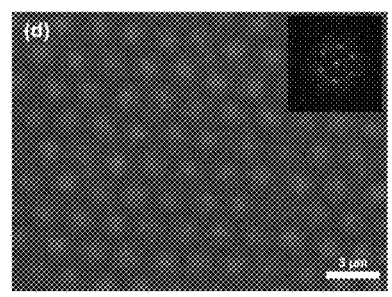 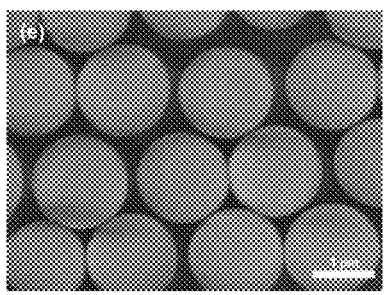
FIG. 2D FIG. 2E

SELF-ASSEMBLED STRUCTURES COMPOSED OF MONOMERS OF PEPTIDE NUCLEIC ACID AND TUNABLE PHOTONIC CRYSTALS MADE THEREFROM

RELATED APPLICATIONS

This application is a National Phase of PCT Patent Application No. PCT/IL2016/051134 having International filing date of Oct. 19, 2016, which claims the benefit of priority under 35 USC § 119(e) of U.S. Provisional Patent Application No. 62/243,192 filed on Oct. 19, 2015. The contents of the above applications are all incorporated by reference as if fully set forth herein in their entirety.

FIELD AND BACKGROUND OF THE INVENTION

The present invention, in some embodiments thereof, relates to material science and, more particularly, but not exclusively, to structures composed of self-assembled peptide nucleic acid (PNA) monomers, to processes of generating same, to photonic crystals made therefrom and to uses thereof.

Molecular self-assembly is the spontaneous organization of molecular units into ordered structures as a result of local interactions among the molecules themselves, without any external intervention. The concept of self-assembly is a widely applied approach in the field of nanotechnology for the bottom-up fabrication of novel nanoscopic and macroscopic elements from natural or synthetic building blocks.

Peptide nucleic acid (PNA) is an artificially synthesized polymer that was first described by Peter Nielsen's and Ole Buchardt's research groups in 1992. In its basic form, it is an oligonucleotide analog in which the phosphate ribose ring of DNA is replaced by a polyamide backbone composed of repeating N-(2-aminoethyl)glycine units linked by peptide bonds. Methylene carbonyl linkages connect between the central amine of the backbone and the various nucleobases. The configuration and the intramolecular distances between neighboring bases, as imposed by the peptide-like backbone, are equal to those in natural nucleic acids.

PNAs have been used in the formation of ordered nano- and micro-sized self-assembled architectures, yet only as a template or as a conjugate to the self-assembled structure in order to gain specific recognition properties.

Guanine is one of the most important building blocks in nature. The intrinsic properties of guanine allow it to form multiple non-covalent interactions including electrostatic interactions, hydrogen bonds, hydrophobic interactions, and aromatic stacking. Therefore, despite being one of the simplest building blocks of natural systems, guanine serves as a key component in diverse range of both natural and designed supramolecular architectures.

Guanine-rich nucleic acid sequences, for instance, the human telomeric DNA, are known to form tetrameric clusters termed G-quadruplexes, which are of great interest in the fields of therapeutics and biosensing [J. T. Davis, *Angew. Chem. Int. Ed. Engl.* 2004, 43, 668]. Synthetic guanosine analogs were shown to assemble into nano-ribbons and macrocycles possessing semiconductive properties [J. T. Davis, G. P. Spada, *Chem. Soc. Rev.* 2007, 36, 296].

Guanine is also used to produce functional assemblies in natural systems. Anhydrous guanine crystal nano-plates consist pigment cells, denoted iridophores or guanophores, in the skin of a wide range of animals of distinct taxonomic groups [see, for example, Gur et al., *J. Am. Chem. Soc.* 2014, 136, 17236; Gur et al., *Angew. Chemie* 2015, doi: 10.1002/anie.201502268; Gur et al., *Angew. Chem. Int. Ed. Engl.* 2013, 52, 388; Levy-Lior et al., *Adv. Funct. Mater.* 2010, 20, 320; Gur et al., *Angew. Chemie* 2013, 125, 406].

The stacked arrangement of the guanine crystalline plates acts as a high quality reflector that generates structural colors. This efficient color formation is based on the very high refractive index of the guanine crystals, 1.83 in the reflecting direction [P. J. Herring, *Comp. Biochem. Physiol. Part A Physiol.* 1994, 109, 513]. The reflecting structures serve, for example, for camouflage, communication and thermoregulation as in the case of fish and chameleons. Similar architectures were found also in the ocular tapeta lucida tissue of some spiders, marine fauna, crocodiles, cats and other animals with shiny mirror-reflecting eyes.

The above-described guanine-based arrays are described in the art as nano-scale photonic structures found in nature [see, for example, P. Vukusic, *Phys. World* 2004, 17, 35; P. Vukusic, J. R. Sambles, *Nature* 2003, 424, 852; M. Xiao, A. Dhinojwala, M. Shawkey, *Opt. Express* 2014, 22, 14625; Li et al., *Nat. Commun.* 2015, 6, 6322].

A photonic structure, or photonic crystal, is a periodic optical structure that affects the motion of photons in much the same way that ionic lattices affect electrons in solids. Photonic crystals affect electromagnetic wave propagation in the same way that the periodic potential in a semiconductor crystal affects electron motion by defining allowed and forbidden electronic energy bands.

Photonic crystals contain regularly repeating regions of high and low dielectric constant. Photons (behaving as waves) propagate through this structure or don't—depending on wavelength. Wavelengths that propagate are called modes, and groups of allowed modes form bands. Disallowed bands of wavelengths are called photonic band gaps. This gives rise to distinct optical phenomena, such as inhibition of spontaneous emission, high-reflecting omni-directional mirrors, and low-loss-waveguiding.

The spectral positions of these bands are dependent on the distance between the periodic modulations in the crystal. The periodicity of the photonic crystal structure must be around half the wavelength of the electromagnetic waves to be diffracted. This is about 200 nm (blue) to about 350 nm (red) for photonic crystals that operate in the visible part of the spectrum, or even less, depending on average index of refraction. The repeating regions of high and low dielectric constant must, therefore, be fabricated at this scale, making the task of fabricating photonic crystal non-trivial.

A photonic crystal may have a one-, two-, or three-dimensional (3-D) periodic structure. A 1-D photonic crystal has a periodic multilayer structure, also referred to as a Bragg mirror. Such a structure has a reflectance peak for incident light in only one direction—perpendicular to the layers. A 2-D photonic crystal has a modulation in only two dimensions. Such a structure has a reflectance peak for incident light in two directions—along the plane of the repeating units. A 3-D photonic crystal has an ordered periodicity in all three dimensions. Such a structure has reflectance peaks for incident light in all directions.

Although the unique and elegant guanine organization can be exceptionally advantageous for diverse optical applications that require controlling and manipulating light, vivid colors, camouflage and even dynamic color tuning, attempts to grow guanine nano-plates in-vitro resulted in thicker and irregular-shaped crystals with a different morphological anisotropy [Levy-Lior et al., *Cryst. Growth Des.* 2008, 8, 507].

Other biological coloration designs have inspired in recent years the fabrication of various photonic structures via artificial materials [see, for example; Zhao et al., Chem. Soc. Rev. 2012, 41, 3297; Kolle et al., Adv. Mater. 2013, 25, 2239; England et al., Proc. Natl. Acad. Sci. U.S.A. 2014, 111, 15630; Xiao et al., ACS Nano 2015, 9, 5454; R. Potyrailo, R. R. Naik, Annu. Rev. Mater. Res. 2013, 43, 307].

WO 2014/178057 describes that guanine-containing short sequences of peptide nucleic acids (PNAs) can self-assemble into ordered structures which exhibit unique optical properties. See also, Berger et al., Nat. Nanotechnol. 2015, 10, 353; and Adler-Abramovich et al., Nat. Chem. Biol. 2012, 8, 701.

Additional background art includes Achim et al., "Peptide Nucleic Acids" in Wiley Encyclopedia of Chemical Biology, 2008, pp. 1-10; Bonifazi et al., Artificial DNA: PNA & XNA 3:3, 112-122, July-December 2012; Teyssier et al., Nat. Commun. 2015, 6, 6368; U.S. Pat. No. 8,309,514; G. Fichman, E. Gazit, Acta Biomater. 2014, 10, 1671; and Fleming et al., Chem. Commun. (Camb). 2013, 49, 10587.

SUMMARY OF THE INVENTION

The present inventors have uncovered that guanine-based peptide nucleic acid (PNA) monomers, particularly guanine-based PNA monomers, can self-assemble into ordered structures, for example, upon contacting an aqueous solution, and that these ordered structures can further organize into a packed mono-layer with hexagonal symmetry, that can act as a tunable photonic crystal, for example, in response to a change in the osmolarity of a solution that contacts the crystal.

According to an aspect of some embodiments of the present invention there is provided an ordered structure composed of a plurality of peptide nucleic acid (PNA) monomers, at least a portion of the monomers are N-protected PNA monomers having at least one amine group capped by an N-protecting moiety.

According to some of any of the embodiments described herein, each of the PNA monomers is an N-protected monomer.

According to some of any of the embodiments described herein, at least a portion of the N-protected PNA monomers have two amine groups each being independently capped by an N-protecting moiety.

According to some of any of the embodiments described herein, in at least a portion of the N-protected PNA monomers, the N-protecting moiety is an aromatic N-protecting moiety.

According to some of any of the embodiments described herein, each of the N-protected PNA monomers has two amine groups each being independently capped by an aromatic N-protecting moiety.

According to an aspect of some embodiments of the present invention, there is provided an ordered structure composed of a plurality of peptide nucleic acid (PNA) monomers, at least a portion of the monomers are modified PNA monomers comprising at least one aromatic moiety attached to a backbone, a nucleobase and/or a nucleobase linkage unit of the PNA monomer.

According to some of any of the embodiments described herein, in at least a portion of the modified PNA monomers, each of the modified PNA monomers comprise at least two aromatic moieties attached to the backbone, the nucleobase and/or to the linkage unit.

According to some of any of the embodiments described herein, in at least a portion of the modified PNA monomers, each of the modified PNA monomers comprises at least one aromatic moiety as a substituent of an amine group that forms a part of the backbone or the nucleobase.

According to some of any of the embodiments described herein, each of the modified PNA monomers is independently represented by Formula I:

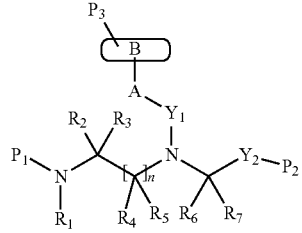

Formula I wherein each of the variables is as defined hereinafter, provided that at least one of $P_1$, $P_2$ and $P_3$ is the N-protecting moiety or is an aromatic moiety.

According to some of any of the embodiments described herein, each of the PNA monomers in the plurality of monomers independently comprises a nucleobase selected from the group consisting of guanine, adenine, thymine, cytosine and an analog of any of the foregoing.

According to some of any of the embodiments described herein, at least a portion of the PNA monomers comprises guanine or an analog thereof as the nucleobase.

According to some of any of the embodiments described herein, each of the PNA monomers comprises a guanine or an analog thereof.

According to some of any of the embodiments described herein, each of the PNA monomers is a modified PNA monomer represented by the formula:

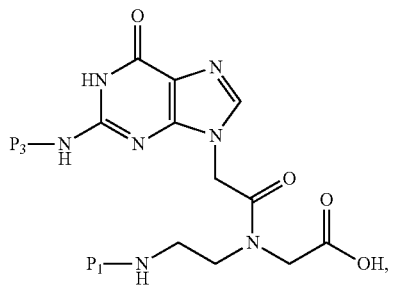

with $P_1$ and $P_3$ being as defined herein in any of the respective embodiments.

According to some of any of the embodiments described herein, each of the PNA monomers is a modified PNA monomer represented by the Formula:

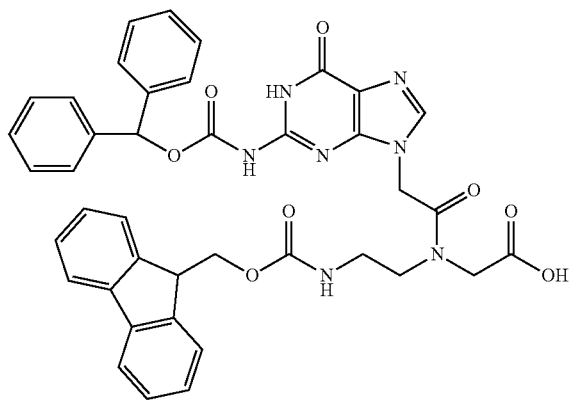

According to some of any of the embodiments described herein, the structure is a substantially spherical structure.

According to some of any of the embodiments described herein, a diameter of the spherical structure ranges from 0.1 to 10 microns.

According to some of any of the embodiments described herein, a structure as described herein is generated by contacting the plurality of PNA monomers, or a solution comprising the PNA monomers and an organic solvent, with an aqueous solution, at a concentration lower than 50 mg of the PNA monomer per ml of the aqueous solution.

According to some of any of the embodiments described herein, a concentration of the monomers in the aqueous solution ranges from 1 mg/ml to 10 mg/ml.

According to some of any of the embodiments described herein, the aqueous solution has a neutral pH.

According to an aspect of some embodiments of the present invention, there is provided a process of preparing an ordered structure composed of a plurality of PNA monomers, the process comprising subjecting a plurality of PNA monomers, at least a portion of which being modified PNA monomers as defined herein in any of the respective embodiments, to conditions which favor formation of the ordered structure.

According to some of any of the embodiments described herein, the conditions favor self-assembly of the plurality of PNA monomers.

According to some of any of the embodiments described herein, the conditions comprise contacting the plurality of PNA monomers with an aqueous solution, to thereby obtain an aqueous solution comprising the plurality of PNA monomers.

According to some of any of the embodiments described herein, the conditions further comprise heating the aqueous solution, and then cooling to room temperature.

According to some of any of the embodiments described herein, the conditions comprise dissolving the PNA monomers in an organic solvent, so thereby obtain an organic solution comprising the plurality of PNA monomers, and diluting the organic solution with an aqueous solution.

According to some of any of the embodiments described herein, the aqueous solution has a neutral pH.

According to some of any of the embodiments described herein, a concentration of the plurality of PNA monomers in the aqueous solution is lower than 50 mg/ml.

According to some of any of the embodiments described herein, a concentration of the plurality of PNA monomers in the aqueous solution ranges from 0.1 to 10 mg/ml.

According to an aspect of some embodiments of the present invention, there is provided an ordered structure prepared by a process as defined herein in any of the respective embodiments.

According to an aspect of some embodiments of the present invention, there is provided a composition comprising a plurality of structures as defined herein in any of the respective embodiments.

According to some of any of the embodiments described herein, the composition further comprises a carrier.

According to some of any of the embodiments described herein, the carrier is a liquid carrier and the structures are dispersed or suspended in the carrier.

According to some of any of the embodiments described herein, the carrier is a solid carrier and the structures are deposited onto a surface of the carrier.

According to some of any of the embodiments described herein, the carrier is a solid carrier and the structures are incorporated in and/or on the solid carrier.

According to an aspect of some embodiments of the present invention, there is provided a photonic crystal comprising a plurality of structures as defined in any one of claims 1-20 and 29, the structures being periodically arranged so as to exhibit a periodic modulation in a refractive index thereof.

According to some of any of the embodiments described herein, the structures are arranged to form a two-dimensional ordered array.

According to some of any of the embodiments described herein, the array features a hexagonal symmetry arrangement.

According to some of any of the embodiments described herein, the photonic crystal is characterized by a reflectance wavelength range, wherein the periodic modulation of the refractive index is responsive to an external stimulus and the reflectance wavelength range is shifted in response to the external stimulus.

According to some of any of the embodiments described herein, the external stimulus comprises a chemical change in an environment of the crystal.

According to some of any of the embodiments described herein, the external stimulus comprises a change in the osmolarity of a solution contacting the crystal.

According to some of any of the embodiments described herein, the external stimulus comprises a change in a dielectric constant of a solution contacting the crystal.

According to some of any of the embodiments described herein, the external stimulus comprises a mechanical deformation of a solid matrix contacting the crystal.

According to an aspect of some embodiments of the present invention, there is provided an article-of-manufacturing comprising a matrix and a photonic crystal as described herein in any one of the respective embodiments incorporated in and/or on the matrix.

According to an aspect of some embodiments of the present invention, there is provided a method of tuning a reflectance wavelength range of a photonic crystal as described herein in any of the respective embodiments, the method comprising changing an osmolarity of an aqueous solution which contacts the photonic crystal.

According to some of any of the embodiments described herein, the changing comprises adding a water-soluble salt to the aqueous solution.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
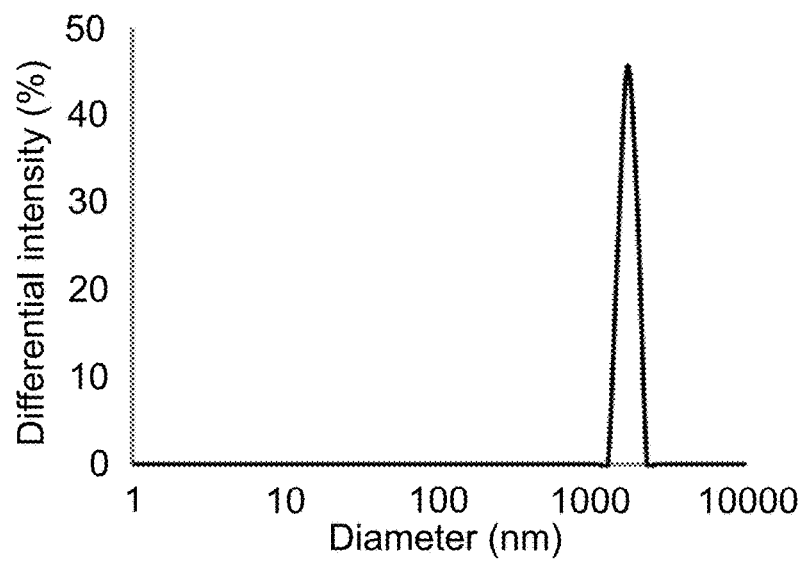
Figure 1B:
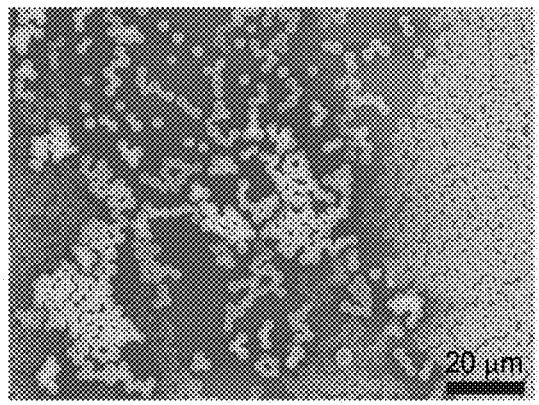
Figure 1C:
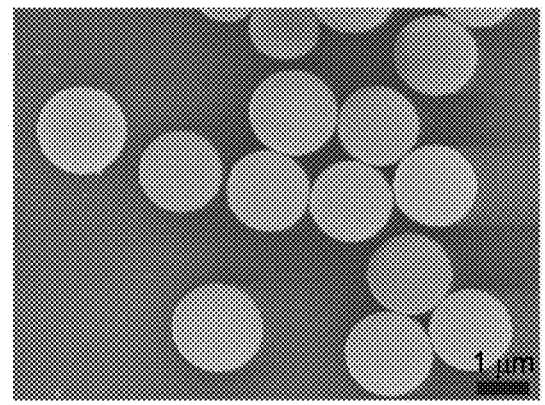

FIGS. 1A-C present a DLS analysis of the self-assembled spheres formed from Fmoc-G-(Bhoc)-aeg-OH, showing a highest differential intensity observed for 1.7 μm (FIG. 1A) and SEM micrographs of the self-assembled spheres at two magnifications (FIGS. 1B and 1C).

FIGS. 2A-E present an image of a colored layer formed at the interface of the solution and the air after spheres of Fmoc-G-(Bhoc)-aeg-OH self-assembled (FIG. 2A), and an image showing that this colored layer can be deposited on a solid substrate by gently drawing the excess solution from underneath using a syringe (FIG. 2B). In FIG. 2C, a light microscopy image of the deposited colored layer is presented and reveals a tightly-packed monolayer of spheres, and a higher magnification of this layer (FIG. 2D) shows the hexagonal symmetry arrangement of the spheres, with the inset presenting a fast Fourier transform (FFT) analysis of the image, indicating hexagonal symmetry as well. FIG. 2E presents SEM micrograph of the hexagonal organization of the spheres in a deposited layer.

Figure 3A:
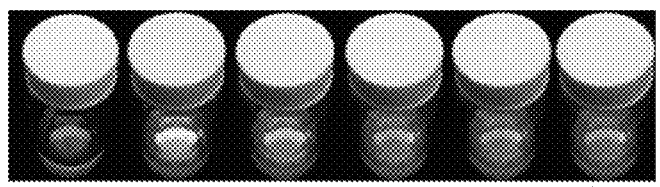
Figure 3B:
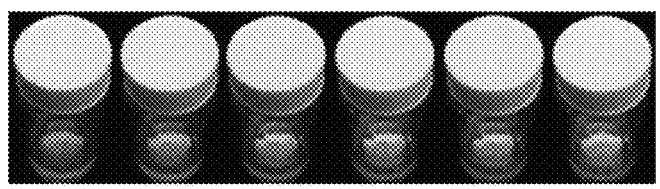
Figure 3C:
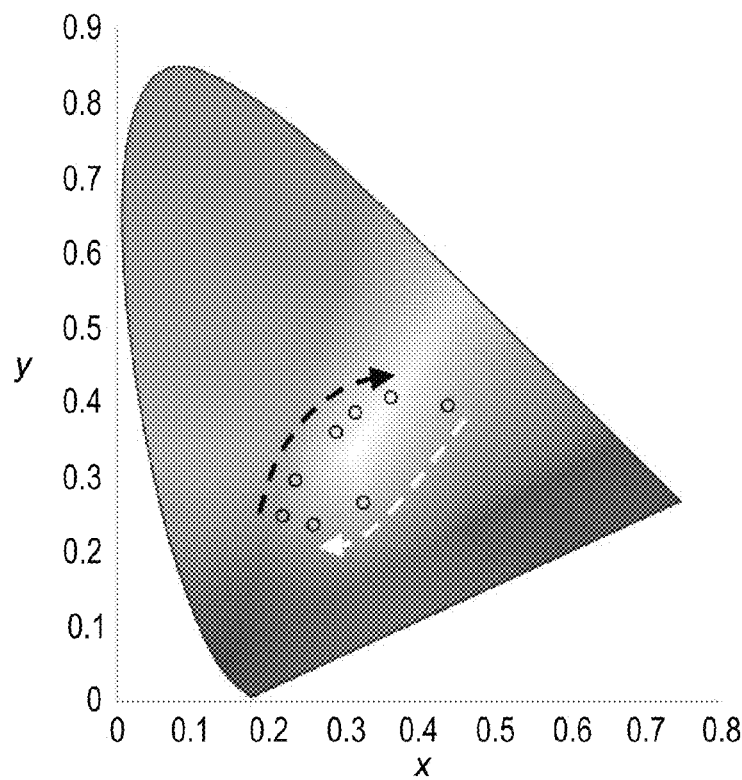
Figure 3D:
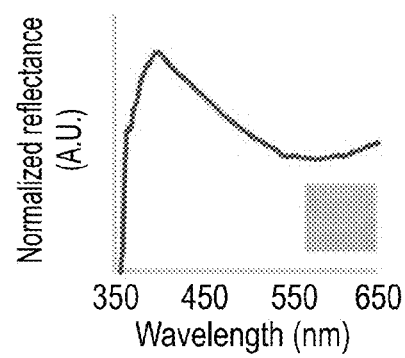
Figure 3D:
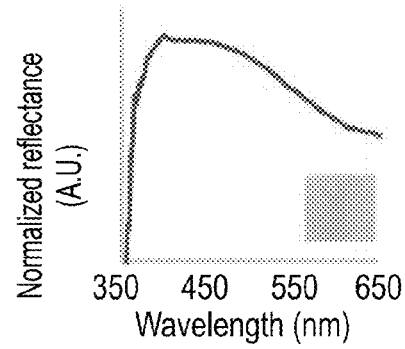
Figure 3D:
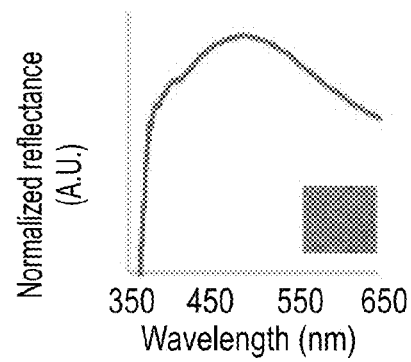
Figure 3D:
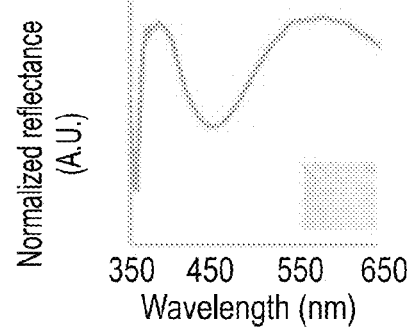

FIGS. 3A-D show salt-induced color changes in the guanine-based PNA photonic crystals. FIGS. 3A-B present six consecutive snapshots of the same glass vial containing a guanine-based PNA photonic crystal before (FIG. 3A) and after (FIG. 3B) the addition of 75 mg ml$^{-1}$ NaCl, over time. FIG. 3C presents the time evolution of the change in color before and after NaCl addition, as presented on the CIE color space. The white arrow indicates the change in color before the addition of NaCl and the black arrow indicates the change after the addition NaCl to the solution. FIG. 3D are graphs showing the spectra of reflected light recorded for PNA photonic crystals deposited on glass slides at different stages of color evolution following the addition of NaCl. The insets are optical images of the coated slides. The width of each image is 3.3 mm.

FIGS. 4A-D present a background art image of Panther chameleon (photographed by Florence Ivy, Flickr) (left) and a background art TEM micrograph of the guanine nanocrystals lattice from panther chameleon iridophores in a relaxed state [taken from Teyssier et al., *Nat. Commun.* 2015, 6, 6368] (right). b) (FIG. 4A); an image of deposited guanine-based PNA photonic crystals (left) and a SEM micrograph of the PNA spheres (right) according to embodiments of the present invention (FIG. 4B), showing that the PNA photonic crystals are arranged in a similar pattern to the biogenic guanine nanocrystals in the chameleon; and a model representation of the PNA sphere lattice before (FIG. 4C) and following (FIG. 4D) the addition of salt, showing that the highly organized array is geometrically altered following salt addition, resulting in a visible shift in the reflected wavelengths.

DESCRIPTION OF SPECIFIC EMBODIMENTS OF THE INVENTION

The present invention, in some embodiments thereof, relates to material science and, more particularly, but not exclusively, to structures composed of self-assembled peptide nucleic acid (PNA) monomers, to processes of generating same, to photonic crystals made therefrom and to uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

WO 2014/178057, Berger et al., *Nat. Nanotechnol.* 2015, 10, 353, and Adler-Abramovich et al., *Nat. Chem. Biol.* 2012, 8, 701, describe that guanine-containing short sequences of peptide nucleic acids (PNAs) can self-assemble into ordered structures which exhibit optical properties. Therein, it is also taught that guanine-containing PNA monomers self-assemble into a spherical structure when placed in an alkaline solution.

While further exploring the self-association and organization into supramolecular assemblies of PNA monomers, the present inventors have uncovered that peptide nucleic acid (PNA) monomers, particularly N-protected PNA monomers, and more particularly, N-protected guanine-based PNA monomers, can self-assemble into stable ordered structures, for example, upon contacting an aqueous solution, and that these ordered structures can further organize into a tightly-packed mono-layer with hexagonal symmetry, that can act as a tunable photonic crystal, for example, in response to a change in the osmolarity of a solution that contacts the crystal.

In comparison to currently known methodologies for producing photonic crystals, such as lithography and uniquely designed cross-linked polymers, the newly described methodology does not involve usage of organic solvents, initiators or surfactants or specialized techniques, not metallic reagents and/or polymeric materials. The methodology, according to the present embodiments, can be practiced while using water and organic small molecules, and a facile, inexpensive and environmentally friendly process, rendering it highly attractive for use in various technological applications.

According to an aspect of some embodiments of the present invention there is provided a structure comprising a plurality of monomers of a peptide nucleic acid (PNA), wherein at least a portion of these monomers are modified PNA monomers, as described herein.

In some embodiments, the PNA monomers (e.g., modified PNA monomers) are arranged in an ordered structure, as defined herein.

In some embodiments, the plurality of PNA monomers, including modified PNA monomers as described herein, self-assemble to form an ordered structure, as defined herein.

In some embodiments, the structure is a self-assembled, ordered structure formed of the plurality of PNA monomers, including modified PNA monomers, as described herein.

In some embodiments, there is provided a composition-of-matter comprising a plurality of monomers of a peptide nucleic acid (PNA), at least a portion of said plurality of monomers are modified PNA monomers, as defined herein, at least a portion of said modified PNA monomers are arranged together (self-assembled) so as to form an ordered structure as described herein.

In some embodiments, there is provided a composition comprising a plurality of ordered structures as defined herein. In some embodiments, the composition further comprises a carrier, e.g., a liquid carrier (for example, an aqueous solution such as water) in which the structures are dispersed, or suspended. In some embodiments, the composition further comprises a solid carrier onto which the structures are deposited.

In some embodiments, a portion of the ordered structures are arranged so as to form crystalline structure. In some of these embodiments, the arranged structures form a photonic crystal, and in some embodiments, the photonic crystal is a tunable photonic crystal. In some embodiments, a reflectance wavelength range of the photonic crystal changes in response to a change in the osmolarity of a solution contacting the photonic crystal.

The Peptide Nucleic Acid (PNA) Monomers:

In any of the aspects and embodiments of the present invention, the terms "peptide nucleic acid monomers", "PNA monomers", "monomers of PNA", "PNA building blocks" and "PNA backbone units" and any grammatical diversion thereof, are used interchangeably and describe a N-(2-aminoethyl)glycine unit, or an analog thereof, as described herein, having a nucleobase (or an analog thereof, as described herein) connected to the central amine thereof, directly or indirectly, e.g., via a methylene carbonyl linkage or variations thereof, as described herein. These terms are used herein to describe a single N-(2-aminoethyl)glycine unit or analog thereof to which a single nucleobase or an analog thereof is attached. The moiety linking the nucleobase to the backbone unit of the PNA is referred to herein also as nucleobase linkage unit or a nucleobase linking moiety.

A chemical structure of a commonly used, N-(2-aminoethyl)glycine-based backbone unit of PNAs is as follows:

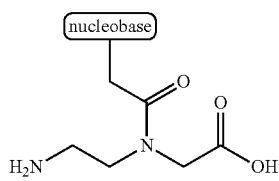

A PNA monomer featuring such a chemical structure and a naturally-occurring nucleobase is also referred to herein as a non-modified PNA monomer.

Embodiments of the present invention relate to a plurality of PNA monomers in which at least a portion of the PNA monomers in the plurality of PNA monomers are modified PNA monomers.

Herein, the term "modified PNA monomer" encompasses peptide nucleic acid monomer as described herein, in which one or more of the nucleobase moiety, the N-(2-aminoethyl) glycine unit and the nucleobase linkage unit, is/are modified, that is is/are analog(s) or variation(s) or modification(s) of a nucleobase and/or the a N-(2-aminoethyl)glycine unit and/or a methylene carbonyl linkage, respectively, and/or which includes additional appended groups or agents which may be attached to the C- and/or N-terminus or to any other position within the nucleobase, the N-(2-aminoethyl)glycine unit and/or the nucleobase linkage unit of a PNA monomer.

Herein, PNA monomers modified so as to include a backbone unit other than a N-(2-aminoethyl)glycine unit and/or a nucleobase linkage unit other than methylene carbonyl are referred to as "backbone-modified PNA monomers", and PNA monomers modified by including a nucleobase analog are referred to as "nucleobase modified-PNA monomers".

The following describes exemplary backbone-modified PNA monomers, which are suitable for use as one or all of the PNA monomers in the plurality of PNA monomers as described herein.

I. Backbone modified PNA monomers in which alkylene (e.g., methylene) group(s) is/are inserted into the N-(2-aminoethyl)glycine unit and/or the nucleobase linkage unit. See, for example, Formula I hereinbelow, in which A is an alkylene chain other than methylene (e.g., ethylene) and/or in which n is other than 0.

II. Backbone modified PNA monomers in which methylene or alkylene bridges that connect the various positions in the N-(2-aminoethyl)glycine unit and/or in the nucleobase linkage are introduced. Such a modification typically forms cyclic moieties within the backbone of the modified PNA monomer. See, for example, Formula I hereinbelow, in which one or more pairs of $R_1$-$R_3$, $R_6$ and $R_7$, and optionally of $R_4$ and $R_5$, if present (when n is other than 0), is/are joined to form one or more cyclic ring(s) (e.g., alicyclic or heteroalicyclic ring).

III. Backbone modified PNAs in which one or more amino acid side chains, which can have R or S configuration, are introduced at the α-position of the N-(2-aminoethyl) glycine unit. Any of the naturally-occurring or artificial amino acid side chains are encompassed by this modification. See, for example, Formula I hereinbelow, in which $R_4$ is an amino acid side chain.

IV. Backbone modified PNAs in which one or more amino acid side chains are introduced at the γ-position of the N-(2-aminoethyl) glycine unit. The side chains can have R or S configuration and can be derived from any of the naturally-occurring or artificial amino acid side chains. See, for example, Formula I hereinbelow, in which $R_3$ and/or $R_5$ (if n is other than 1) is an amino acid side chain.

V. Backbone modified PNA monomers in which the carboxylic acid group is replaced by, for example, a carboxylate ester, a thiocarboxylic acid, a thiocarboxylate ester, a thioamide, a carbamate, a thiocarbamate, a sulfonamide, etc. See, for example, Formula I below in which $Y_2$—$P_2$ is other than C(═O)—OH.

VI. Backbone modified PNA monomers in which the carboxymethylene (methylene carbonyl) nucleobase linkage unit is replaced by, for example, an alkylene, a thiocarboxymethylene, a carbamate methylene, a thiocarbamate methylene, an amide methylene, a thioamide methylene, a sulfonamide methylene, a sulfonate methylene, an ester methylene, a thioester methylene, an aminomethylene, etc. See, for example, Formula I, in which Y1 is other than C═O.

VII. Backbone modified PNAs in which a substituent other than hydrogen is introduced at the α-position, β-position or γ-position of the N-(2-aminoethyl) glycine unit, with exemplary substituents being alkyl, cycloalkyl, aryl, heteroaryl, amine, an aromatic moiety as defined herein, or any other substituent as described herein, or, alternatively, being a functional group or moiety such as, for example, a metal-complexing ligand, a receptor ligand, a hydrophobic moiety or group, a negatively or positively charged moiety or group, etc.

The following describes exemplary nucleobase-modified PNA monomers, which are suitable for use as one or all of the PNA monomers in the plurality of PNA monomers as described herein.

Exemplary nucleobase-modified PNA monomers include PNA monomers in which the nucleobase is an analog of the five naturally occurring bases (adenine (A), guanine (G), cytosine (C), thymine (T) and uracil (U)). Thus, such a modified PNA monomer includes at least one nucleobase analog, for example, as described herein.

Exemplary nucleobase analogs can be collectively represented by Formulae II and III:

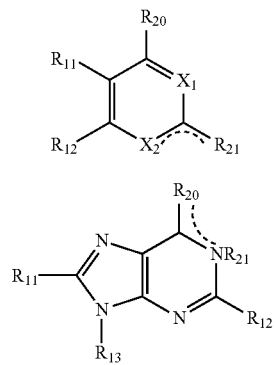

wherein the dashed lines denote a resonating double bond, such that the moiety between $X_2$ and $R_{21}$ in Formula II can be $X_2$=C—$R_{21}$ or $X_2$—C=$R_{21}$, and the moiety between $R_{20}$ and $NR_{21}$ in Formula III can be $R_{20}$=C—$NR_{21}$ or $R_{20}$—C=N— (with $R_{21}$ being absent.

$R_{20}$ and $R_{21}$ in Formulae II and III can each independently be amine, hydroxyl, thiohydroxy, oxo (=O), thioxo (=S), or absent;

$X_1$ and $X_2$ in Formula II can be N or $CR_{14}$; and $R_{11}$-$R_{14}$ can each independently be hydrogen, or any chemical or functional group (e.g., alkyl, cycloalkyl, halo, amine, aryl, heteroaryl, hydroxyl, alkoxy, thiol, thioalkoxy, aryloxy, thioaryloxy, carboxy, amide, thiocarboxy, carbamate, sulfonyl, sulfate, sulfonamide, and any other chemical group).

Exemplary nucleobase analogs include, but are not limited to, 5-fluorouracil; 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine, and 3-nitropyrrole.

Exemplary guanine analogs include, but are not limited to, 1-methylguanine, 2,2-dimethylguanine, 2-methylguanine, and 7-methylguanine.

Additional exemplary nucleobase analogs include, for example pseudo-isocytosine; 2,6-diaminopurine an analog of adenine); and a "guanidine G-clamp" (an analog of cytosine).

The nucleobase analogs as described herein can be combined as bases with any of the backbone-modified PNA monomers described herein, including any embodiments thereof.

Any other nucleobase analogs are also contemplated herein, each in combination with a PNA monomer, or with any of the backbone-modified PNA monomers described herein, including any embodiments and combinations thereof.

Alternatively, any of the backbone modifications described herein can be combined with the five naturally occurring bases (adenine (A), guanine (G), cytosine (C), thymine (T) and uracil (U)).

A modified PNA, according to some embodiments of the invention, can include one or more of above-mentioned backbone and/or nucleobase modifications, at any combination.

In some of any of the embodiments described herein, a modified PNA is a protected PNA, in which one or more of an amine group and a carboxy group (e.g., a carboxylic acid group or a suitable group replacing it, as described herein, e.g., a thiocarboxy group) is capped by a suitable protecting moiety.

In some of any of the embodiments described herein, some or all of the PNA monomers forming the structure are modified PNA monomers which are protected PNA monomers, that is, have one or more protecting moiety capping an amine or carboxy group thereof.

The amine and/or carboxy group capped by a protecting moiety can be a group present in a corresponding non-modified PNA monomer, namely, an amine and/or carboxylic acid at a terminus of the N-(2-aminoethyl)glycine unit, and/or an amine group of a naturally-occurring nucleobase.

The amine and/or carboxy group capped by a protecting moiety can otherwise, or in addition, be a group introduced by modification of one or more of the backbone or nucleobase of a modified PNA monomer, namely, a group that is not present in a non-modified PNA monomer.

In some of any of the embodiments described herein, some or all of the PNA monomers forming the structure are N-protected modified PNA monomers, which comprise at least one amine group in a form of an amine-protected group, in which the amine group is capped by an N-protecting moiety or group (also referred to herein as an amine protecting moiety or group), as defined herein.

Exemplary amine groups which can be capped by a N-protecting group in a protected PNA monomer as described herein can include the terminal amine group of the N-(2-aminoethyl)glycine unit or an analog thereof, an amine group of the nucleobase or an analog thereof, an amine group present in a group replacing the carboxymethylene (methylene carbonyl) nucleobase linkage, an amine group as a substituent of one or more of the α-position, β-position or γ-position of the N-(2-aminoethyl) glycine unit, an amine group replacing the carboxylic group terminus of the N-(2-aminoethyl) glycine unit.

In some embodiments, a modified PNA monomer includes two or more amine groups that are capped by an N-protecting moiety.

In some of any of the embodiments described herein, some or all of the PNA monomers forming the structure are modified PNA monomers which are protected PNA monomers, as described herein, and which comprise at least one carboxy group in a form of a carboxy-protected group, in which the carboxylate or carboxylic acid group is capped by a carboxy-protecting group, as defined herein.

Exemplary carboxylate groups which can be capped by a carboxy-protecting moiety in a protected PNA monomer as described herein can include the terminal carboxylic group of the N-(2-aminoethyl)glycine unit or an analog thereof, a carboxylate group of the nucleobase or an analog thereof, an carboxylate group as a substituent of one or more of the α-position, β-position or γ-position of the N-(2-aminoethyl) glycine unit, a carboxylate group replacing the amine terminus of the N-(2-aminoethyl) glycine unit.

In some embodiments, a modified PNA monomer includes two or more protecting moieties, at least one of which is an N-protecting moiety and at least another one is a carboxy protecting moiety.

In some embodiments, a modified PNA monomer includes at least one, preferably at least two, aromatic protecting moiety or moieties, which can be one, two or more amine-protecting (N-protecting) moieties, one, two or more carboxy protecting moieties, or a combination of one or more amine-protecting moiety(ies) and one or more carboxy protecting moiety(ies), as described herein.

In some of any of the embodiments described herein, one or more of the protecting moieties, whether an amine-protecting moiety or a carboxy-protecting moiety, is an aromatic protecting moiety.

In some of any of the embodiments described herein, two or more of the protecting moieties, whether an amine-protecting moiety or a carboxy-protecting moiety, are aromatic protecting moieties.

In some of any of the embodiments described herein, two or more of the protecting moieties are amine-protecting moieties and each is independently an aromatic protecting moiety.

In some of these embodiments, the aromatic amine-protecting moieties can be the same or different, and in some embodiments, the aromatic amine-protecting moieties are different.

Whenever the protected PNA monomer includes two or more amine-protecting groups or two or more carboxy-protecting groups, the protecting groups can the same or different.

Herein throughout, a "protecting moiety", which is also referred to herein interchangeably as a "protecting group" describes a chemical moiety that is attached to a chemical group, such as amine or carboxylic acid, to thereby change or mask the chemical properties the chemical group, for example, by masking the charge of the chemical group or by altering its reactivity towards chemical interactions (e.g., by rendering the chemical group less prone to, or by diminishing its participation in, chemical reactions with other groups).

Examples of moieties suitable for modification of amine and carboxylate groups can be found, for example, in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996).

Representative examples of N-protecting moieties, suitable for modification of amine group, include, but are not limited to, formyl, acetyl (also denoted herein as "Ac"), trifluoroacetyl, benzyl, naphthalenyl, benzyloxycarbonyl (also denoted herein as "Cbz"), benzhydryloxycarbonyl (also denoted "Bjoc"), tert-butoxycarbonyl (also denoted herein as "Boc"), trimethylsilyl (also denoted "TMS"), 2-trimethylsilyl-ethanesulfonyl (also denoted "SES"), trityl and substituted trityl groups, phthalimide, allyloxycarbonyl, 9-fluorenylmethyloxycarbonyl (also denoted herein as "Fmoc"), and nitro-veratryloxycarbonyl ("NVOC").

Representative examples of carboxy-protecting moieties, suitable for modification of carboxylates and are carboxy-containing groups, are typically moieties that lead to acylation of the carboxy group and include, but are not limited to, benzyl and trityl ethers as well as alkyl ethers, tetrahydropyranyl ethers, trialkylsilyl ethers, allyl ethers, monomethoxytrityl and dimethoxytrityl. Alternatively the —COOH group may be modified to an amide group, thioamide group, and any of the other groups described herein for modified PNA monomers.

N-protecting moieties and carboxy-protecting moieties as described herein can be divided also into aromatic and non-aromatic protecting moieties.

According to some embodiments of the present invention, at least a portion of the PNA monomers are modified by one or more aromatic protecting moieties, which can be N-protecting moieties or carboxy-protecting moieties, as described herein.

Representative examples of aromatic N-protecting moieties include, without limitation, fluorenylmethyloxycarbonyl (Fmoc), benzyl, naphthalenyl, benzyloxycarbonyl (also denoted herein as "Cbz"), benzhydryloxycarbonyl (also denoted "Bjoc"), trityl and substituted trityl groups, and moieties containing naphthalene, azobenzene, pyrene and phthalimide.

Representative examples of aromatic carboxy protecting moieties include, without limitation, benzyl, benzyloxycarbonyl (Cbz), trityl and substituted trityl groups.

According to some of any of the embodiments described herein, a modified PNA monomer is a PNA monomer to which an aromatic moiety is attached. Such a modified PNA monomer can be modified by any one of the modifications as described herein, as long as one or more aromatic moiety/moieties is/are included in its structure.

In some embodiments, the aromatic moiety is attached to one or more positions of the N-(2-aminoethyl) glycine unit or an analog or a modification thereof as described herein, to one or more positions of the nucleobase linkage unit or an analog or a modification thereof as described herein, and/or to one or more positions of the nucleobase or an analog thereof as described herein.

By "aromatic protecting moiety" (aromatic N-protecting moiety or aromatic carboxy-protecting moiety) it is meant a protecting moiety, as defined herein, which comprises one or more aromatic moieties, as defined herein.

Herein the phrase "aromatic moiety" describes a moiety that comprises an aryl, as defined herein. An aromatic moiety can therefore be, for example, an alkyl, or alkylene, or cycloalkyl, substituted by one or more aryls, an amine substituted by one or more aryls, an aryloxy, a thioaryloxy, a carboxylate or carbamate or sulfonate or sulfonamide, and the like, terminating by an aryl or by an alkyl that is substituted by one or more aryls, or by amine substituted by one or more aryls.

In some embodiments, an aromatic moiety is attached to the N-(2-aminoethyl) glycine unit or an analog or a modification thereof as described herein. In these embodiments, the aromatic moiety can be attached to the amine moiety at the N-terminus of the unit, to the carboxy group at the C-terminus of the unit, to an amine group replacing the carboxy group at the C-terminus of the unit, and/or be a substituent of one or more of the carbons of the ethylene or any other alkylene chain in the unit.

In terms of Formula I, in these embodiments, an aromatic moiety as described herein can be any one or more of $P_1$, $P_2$ and $R_1$-$R_7$.

In some embodiments, an aromatic moiety is attached to a nucleobase analog, for example, as a substituent of an amine moiety of the nucleobase or an analog thereof (see, e.g., $R_{20}$ in Formula II or III), and/or as a substituent of the ring (see, e.g., $R_{11}$-$R_{14}$ in Formula II or III hereinabove). Such an aromatic moiety is denoted as $P_3$ in Formula I.

In some embodiments, a modified PNA monomer comprises at least two aromatic moieties, and in some of these embodiments, a modified PNA monomer comprises one or more aromatic moieties attached to the N-(2-aminoethyl) glycine unit and one or more aromatic moieties attached to the nucleobase, forming a nucleobase analog.

Exemplary modified PNA monomers as described herein can be collectively represented by Formula I:

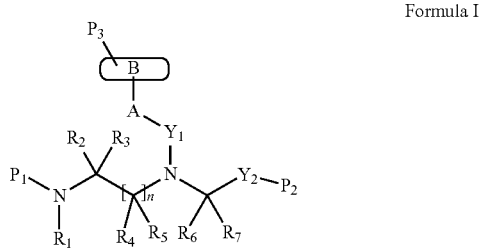

Formula I wherein:

B is a nucleobase or an analog thereof, as described herein in any one of the respective embodiments;

$P_3$ is absent, or is an N-protecting group capping an amine group of the nucleobase or an analog thereof, or is an aromatic moiety attached to the nucleobase or an analog thereof, as described herein in any one of the respective embodiments;

A is substituted or unsubstituted alkylene or absent;

$Y_1$ is selected from C=O, C=S, CRaRb, C=NRa, —NRa-, C(=O)O, C(=S)O, C(=S)S, C(=O/S)NRa, NRaC(=O/S), O/S—C(=O/S)NRa, NRaC(=O/S)—O/S, S(=O)$_2$, S(=O), S(=O/S)NRa, and NRaS(=O/S), with Ra and Rb being each independently selected from hydrogen, alkyl, cycloalkyl, aryl and heteroaryl, or is an aromatic moiety as described herein, or $Y_1$ is absent;

n is an integer that ranges from 0 to 4 (being 0, 1, 2, 3 or 4);

$R_1$-$R_7$ are each independently selected from hydrogen, alkyl, cycloalkyl, aryl, heteroaryl, hydroxy, alkoxy, thiol, thioalkoxy, aryloxy, thioaryloxy, amine, carboxy, amide, thiocarboxy, carbamate, sulfonyl, sulfate, sulfonamide, and the like, or an aromatic moiety, as described herein in any one of the respective embodiments, or, alternatively, two or more of $R_1$-$R_7$ are joined together to form a cyclic moiety (e.g., an alicyclic or heteroalicyclic moiety, as defined herein);

$Y_2$ is C=O, C=S, CRaRb, C=NRa, —NRa-, C(=O)O, C(=S)O, C(=S)S, C(=O/S)NRa, NRaC(=O/S), O/S—C(=O/S)NRa, NRaC(=O/S)—O/S, S(=O)$_2$, S(=O), S(=O/S)NRa, and NRaS(=O/S), with Ra and Rb being each independently selected from hydrogen, alkyl, aryl and cycloalkyl, or is an aromatic moiety as described herein in any one of the respective embodiments;

$P_2$ is selected from hydrogen, alkyl, cycloalkyl, aryl, and heteroaryl, or is an aromatic moiety as described herein in any one of the respective embodiments, or, alternatively, $Y_2$ and $P_2$ form together a carboxylate group capped by a carboxy-protecting group or an amine group capped by an N-protecting group, as described herein in any one of the respective embodiments; and $P_1$ is selected from hydrogen, alkyl, cycloalkyl, aryl, heteroaryl or is an N-protecting group or is an aromatic moiety, as described herein in any one of the respective embodiments.

In some embodiments, at least one of $P_1$, $P_2$ and $P_3$ is an N-protecting group, such as an aromatic N-protecting moiety as described herein, or is an aromatic moiety as described herein in any one of the respective embodiments.

In some of any of the embodiments of Formula I, n is 0, $R_1$-$R_7$ are each hydrogen, $P_2$ is hydrogen, and $P_1$ is said N-protecting group. The backbone unit of the PNA monomer according to these embodiments is therefore modified only at the N-terminus by the inclusion of an N-protecting moiety. In some of these embodiments, $P_1$ is an aromatic moiety.

In some of any of the embodiments of Formula I, $P_3$ is an N-protecting group of, or an aromatic moiety attached to, an amine moiety of the nucleobase (see, e.g., $R_{20}$ in Formula II or III). The nucleobase in the PNA monomer according to these embodiments is therefore modified solely to include such a moiety. In some embodiments, the nucleobase is a thus modified adenine, guanine, cytosine or thymine.

In some of any of the embodiments described herein, the nucleobase is guanine or an analog thereof. In some embodiments, the modified guanine has an aromatic moiety or an N-protecting group as described herein attached to the amine substituent of guanine.

Representative examples of modified PNA monomers usable in the context of the present embodiments include, without limitation:

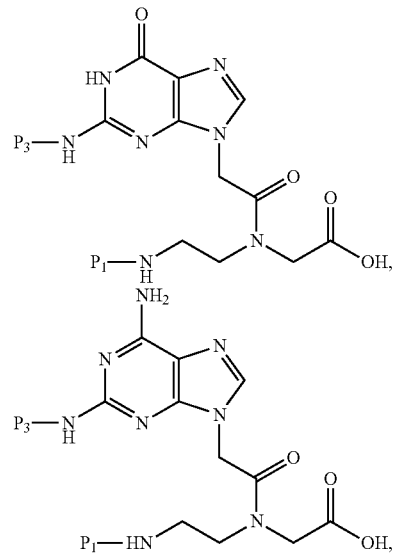

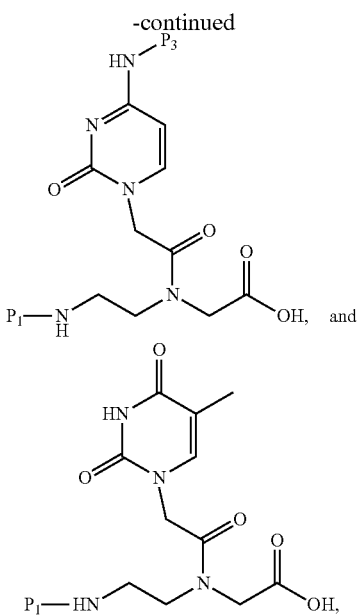

wherein $P_1$ and $P_3$, if present, are each independently selected from hydrogen, alkyl, cycloalkyl, aryl, heteroaryl, an N-protecting moiety or an aromatic moiety, provided that at least one of $P_1$ and $P_3$ is an N-protecting moiety or an aromatic moiety, as described herein in any one of the respective embodiments and any combination thereof.

In some of any of the embodiments described herein, each of the modified PNA monomers is a guanine-based modified PNA monomer, represented by the formula:

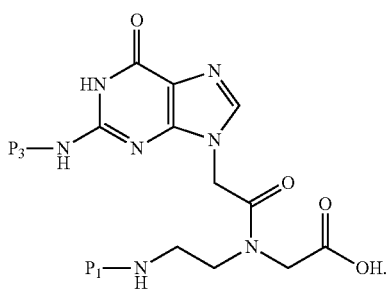

In some embodiments, the guanine-based modified PNA monomer is represented by the Formula:

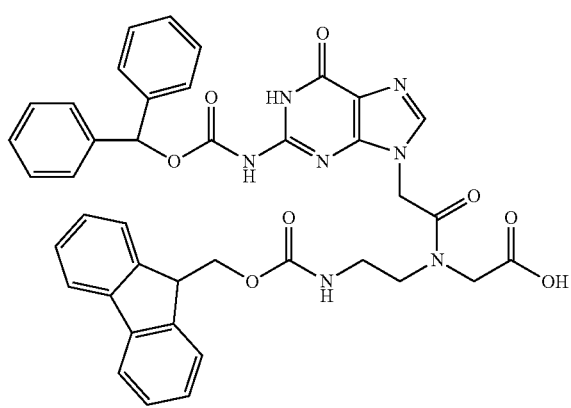 [SMILES: O=C(O)CN(CCNC(=O)OCC1c2ccccc2-c2ccccc21)C(=O)Cn1cnc2c(=O)[nH]c(NC(=O)OC(c3ccccc3)c3ccccc3)nc21]

Any of the PNA monomers and modified PNA monomers described herein can be synthesized by methods well known in the art using, for example, chemistries similar to those used for synthesis of nucleic acids and peptides. PNA backbone units (monomers) used in such syntheses are hybrids of nucleosides and amino acids. PNA monomers may be synthesized using commercially available reagents and equipment or can be purchased from contract manufacturers.

The PNA monomers described herein throughout are denoted by the nucleobase(s) therein (e.g., A, G, C, T, and any combinations thereof), or as X-PNA monomer, or as X-based PNA monomer, with "X" being the nucleobase or an analog thereof.

Some or all of the PNA monomers in the plurality of PNA monomers described in any one of the embodiments herein can be modified PNA monomers, as described herein in any of the respective embodiments.

By "at least a portion" of the monomers being modified PNA monomers, it is meant at least 10%, or at least 20%, or at least 30%, or at least 40%, preferably at least 50%, at least 60%, at least 70%, at least 80%, at least 90%, at least 95%, or substantially all of the PNA monomers are modified PNA monomers.

The plurality of PNAs described in any one of the embodiments herein can include the same or different PNA monomers, including differently modified PNA monomers.

In some of any of the embodiments described herein, at least 80%, or at least 90%, or at least 95%, or at least 99%, or substantially all the PNA monomers in the plurality of PNA monomers are the same, and are modified PNA monomers, as described in any of the respective embodiments.

In some embodiments, when differently modified PNA monomers are included in the plurality of PNA monomers or a portion thereof, the monomers can differ from one another by the nucleobase or an analog thereof. Thus, a plurality of modified PNA monomers can include modified PNA monomers of guanine or an analog thereof, adenine or an analog thereof, cytosine or an analog thereof, thymine or an analog thereof, uracil or an analog thereof, and any combination thereof.

In some embodiments, at least a portion of the modified PNA monomers or of the plurality of PNA monomers are guanine-based modified PNA monomers, as described herein.

In some embodiments, all of the modified PNA monomers or all of the monomers in the plurality of PNA monomers are guanine-based modified PNA monomers, for example, as described herein. The guanine-based modified PNA monomers can be the same or different, and in some embodiments are the same.

In some of any of the embodiments described herein, each of the PNA monomers in the plurality of PNA monomers is a modified PNA monomer which is an N-protected PNA monomer as described herein.

In some embodiments, at least a portion of the N-protected PNA monomers have two amine groups each being independently capped by an N-protecting moiety, which can be the same or different.

In some embodiments, in at least a portion of the N-protected PNA monomers, the N-protecting moiety is an aromatic N-protecting moiety, as described herein.

In some embodiments, each of the N-protected PNA monomers has two amine groups each being independently capped by an aromatic N-protecting moiety as described herein.

In some embodiments, at least a portion, or all, of the plurality of monomers are modified PNA monomers that comprise at least one aromatic moiety, preferably at least two aromatic moieties, attached to a backbone, a nucleobase and/or a nucleobase linkage unit of the PNA monomer, as described herein.

In some embodiments, at least a portion, or all, of the monomers in the plurality of PNA monomers are modified PNA monomers that comprise at least one aromatic moiety as a substituent of an amine group that forms a part of the backbone or the nucleobase, as described herein. Exemplary structures of such modified PNA monomers are presented hereinabove.

The Ordered Structure:

In some embodiments, there is provided a composition-of-matter which comprises the plurality of PNA monomers as described in any of the present embodiments, and any combinations thereof, wherein at least a portion of the monomers are arranged in, or are arranged to form, or are assembled into, an ordered structure.

In some of any of the embodiments of the present invention, the composition-of-matter consists of the plurality of PNA monomers, as described herein.

In some of any of the embodiments of the present invention, at least 50% of the plurality of PNA monomers, as described herein, form, or are arranged to form, an ordered structure as described herein.

In some of any of the embodiments of the present invention, at least 70%, at least 80 5, at least 90%, at least 95%, at least 99%, or essentially all in the PNA monomers in the plurality of PNA monomers, as described herein, form an ordered structure as described herein.

In some embodiments, the composition-of-matter consists of the plurality of PNA monomers, as described herein, in a form of an ordered structure as described herein.

In some embodiments, there is provided an ordered structure, as described herein, composed of a plurality of PNA monomers, as described herein in any of the respective embodiments.

According to some embodiments, the ordered structure is a micrometric structure.

By "micrometric structure" it is meant a structure having at least one dimension at the microscale (0.1-1000 microns, or 1-1000 microns).

By "ordered" structure it is meant that at least 50% of the plurality of PNA monomers, preferably at least 80%, 90% or more, form together a structure, having defined shape and dimension, or a plurality of such structures which can be similar (by at least 80%, or by at least 90%, or by at least 95%, or by at least 99%) to one another in shape and dimension. The PNA monomers in an ordered structure as defined herein are not randomly dispersed in the medium in which the structure is generated, but rather are arranged or assembled in an ordered fashion.

In some embodiments, the PNAs self-assemble to generate the ordered structure and hence the ordered structure is also referred to herein as self-assembled (ordered) structure.

In some embodiments, the ordered structure is generally characterized by a round shape, and can be, for example, an ellipsoid structure, a spherical structure or a cylindrical structure.

In some embodiments, the ordered structure is a generally spherical structure or a plurality of generally spherical structures, whereby in some embodiments, each sphere is in the micrometer scale.

In some embodiments, the ordered structure is generated by contacting a plurality of PNA monomers as described herein with an aqueous solution.

In some embodiments, contacting is effected under conditions which favor formation of the ordered structure (e.g., neutral pH, relatively low concentration of the monomers), as is discussed in further detail under "The process", including any one of the embodiments therein.

The Process:

According to an aspect of some embodiments of the present invention, there is provided a process of preparing a structure according to any one of the embodiments described herein.

In some embodiments, the process is effected by contacting the plurality of peptide nucleic acid monomers, including modified PNA monomers, as described in any of the respective embodiments, with an aqueous solution.

In some embodiments, the contacting is effected under conditions which favor formation of the ordered structure.

In some embodiments, the contacting is effected under conditions which favor self-assembly of the PNA monomers (or at least a portion hereof) so as to form the ordered structure.

Contacting can be effected for a time period that ranges from milliseconds to minutes, although it may also be effected for several hours, and in some cases for days.

In some embodiments, contacting is effected for a time period that ranges from a few seconds to a few minutes (e.g., 0.1-30 minutes, or 0.1-10 minutes).

Contacting can be effected at a temperature that ranges from 40 to 100° C. In some embodiments, contacting is effected while heating to a temperature of from 50 to 100° C., or from 60 to 100° C., or from 80 to 100° C., or from 90 to 100° C. yet any other temperature within the indicated range is also contemplated.

In some embodiments, contacting is effected while heating a solution containing the monomers at a temperature as described herein, and while mixing the solution (e.g., stirring).

In some embodiments, contacting is effected while heating as described herein, until dissolution of the PNA monomers in the solution, and therefore, in some embodiments, the contacting time and temperature depends on the concentration of the PNA monomers in the solution, that is, the contacting time and/or temperature increase as the concentration of the PNA monomers increases.

In some embodiments, the process further comprises removing undissolved PNA monomers from the solution.

In some embodiments, the removal is effected while the solution is still hot.

In some embodiments, the removal is effected by filtration, by filtering the hot solution. Alternatively, removal is effected by any other means for separating the undissolved material from the solution.

In some embodiments, following heating (and mixing), and optionally a removal of undissolved material, the contacting further comprises cooling the solution to room temperature.

In some embodiments, cooling is effected passively by ceasing the heating (e.g., removing the heat source), and allowing the solution to cool.

In some embodiments, cooling is effected actively, by placing the solution in a cooled vessel, for example.

In some embodiments, as cooling progresses, the aqueous solution becomes turbid, and formation of the structure is effected.

In some embodiments, a concentration of the plurality of peptide nucleic acid monomers in the aqueous solution is lower than 50 mg/ml (mg of PNA monomers per ml of the aqueous solution). In some embodiments, a concentration of the PNA monomers ranges from about 0.1 mg/ml to 40 mg/ml, or from about 0.1 mg/ml to 30 mg/ml, or from about 0.1 mg/mg to 20 mg/ml, or from about 1 mg/ml to about 20 mg/ml, or from about 1 mg/ml to about 10 mg/ml, or from about 1 mg/ml to about 5 mg/ml, including any intermediate value or subrange therebetween.

In alternative embodiments, contacting is effected by first dissolving the PNA monomers in an organic solvent, and then contacting the obtained organic solution with an aqueous solution.

In some of these embodiments, contacting is effected at a temperature of from about 0° C. and up to the boiling point of the organic solvent, and is preferably effected at room temperature, and mixing is optional.

The solvent can be, for example, methanol, ethanol, DMSO, DMF, HFIP, and any other solvent in which PNA monomers as described herein are soluble. In some embodiments, the organic solvent is a polar solvent. The polar solvent can be a protic or aprotic solvent. In some embodiments, the organic solvent comprises carboxyl and/or amine groups, which, without being bound by any particular theory, are capable of interacting (e.g., via hydrogen bonds) with the PNA monomers and/or structures made therefrom, and may thereby facilitate the formation of the ordered structures.

In some of these embodiments, a concentration of the PNA solution in the organic solution ranges from about 10 mg/ml to 100 mg/ml, or from about 10 mg/ml to about 80 mg/ml, or from about 10 mg/ml to about 70 mg/ml, or from about 10 mg/ml to about 60 mg/ml, or from about 10 mg/ml to about 50 mg/ml, or from about 20 mg/ml to about 80 mg/ml, or from about 30 mg/ml to about 70 mg/ml, or from about 40 mg/ml to about 60 mg/ml, or is about 50 mg/ml.

In some of these embodiments, contacting of the organic solution with an aqueous solution is effected at a ratio of from about 1 to 10 organic to aqueous solution (by volume; namely, each 1 ml of organic solution is contacted with 9 ml of an aqueous solution to obtain a 10 ml solution) or from about 1 to 20 organic to aqueous solution (by volume), or from about 1 to about 30 organic to aqueous solution (by volume), or from about 1 to about 40 organic to aqueous solution (by volume), or from about 1 to about 50 organic to aqueous solution (by volume), or from about 1 to about 60 organic to aqueous solution (by volume), or from about 1 to about 70 organic to aqueous solution (by volume), or from about 1 to about 80 organic to aqueous solution (by volume), or from about 1 to about 90 organic to aqueous solution (by volume), or from about 1 to about 100 organic to aqueous solution (by volume), or from about 1 to about 5 organic to aqueous solution (by volume).

In some of any of the embodiments described herein for the process, the aqueous solution has a neural pH, namely a pH within a range of from about 6 to about 8, or from about 6.5 to about 7.5, or of about 7.

In some embodiments, the aqueous solution is devoid of a buffer.

In some embodiments, upon contacting the plurality of PNAs with an aqueous solution as described herein and once ordered structures are formed (as can be observed, for example, by electron microscopy such as SEM, or light microscopy), the structures can be isolated from the aqueous solution by e.g., drying.

According to an aspect of some embodiments of the present invention, there is provided an ordered structure composed of a plurality of PNA monomers as described herein, or a composition comprising same, prepared by a process as described herein in any of the respective embodiments.

A Composition:

According to some embodiments of the present invention there is provided a composition which comprises a plurality of ordered structures as described herein.

In some embodiments, the composition further comprises a carrier.

In some embodiments, the carrier is a liquid carrier such as, for example, an aqueous solution or water, and the structures are dispersed or suspended in the carrier.

In some embodiments, the carrier is an aqueous solution in which the nanostructures are generated, as described hereinabove, optionally further comprising an organic solvent, and the composition is a product of a process of generating the structures.

In some embodiments, the carrier is a liquid carrier (e.g., an aqueous solution or water, and the structures are present at the interface of the liquid with its environment (e.g., air).

In some embodiments, the carrier is a solid carrier and the structures are deposited onto a surface of the carrier, or are incorporated in and/or on the carrier.

In some of any of the embodiments described herein, the composition further comprises an additional material which is in association with the structures formed from the PNA monomers.

The association can be a chemical interaction (e.g., a chemical bond such as a covalent bond, an electrostatic bond, a hydrogen bond) or a physical interaction (e.g., encapsulation, entrapment, deposition, absorption, etc.).

By "associated therewith" it is meant that the material (e.g., an agent or moiety) is in chemical or physical interaction with the structures (at least a portion of the structures), whereby in some embodiments, this interaction is not a result of a mere mutual presence in the same environment, mixture, medium or matrix.

Thus, for example, agents or moieties can be associated with the structures, by interacting with functional groups present in the PNA monomers forming the structure via, e.g., covalent bonds, electrostatic interactions, hydrogen bonding, van der Waals interactions, donor-acceptor interactions, aromatic (e.g., $\pi$-$\pi$ interactions), cation-$\pi$ interactions and metal-ligand interactions. These interactions lead to the chemical association of the agent or moiety to the ordered structure.

As an example, various agents or moieties can be attached to the PNAs forming the structure via chemical interactions with functional groups of the backbone unit, or of the nucleobase linkage unit, if present.

Alternatively, various materials and agents can be attached to the ordered structure by physical association such as magnetic interactions, surface adsorption, encapsulation, entrapment, entanglement and the likes.

The material can be a group or moiety chemically attached to one or more of the PNA monomer, which can be attached to the PNA monomers prior to formation of the ordered structure or subsequent to said formation; or can be a material associated with the ordered structure upon or during its formation, optionally via a functional group or moiety included within the PNA monomer, as described herein, or by absorption, deposition, entrapment or encapsulation.

Exemplary materials include, but are not limited to, a conductor material, a semiconductor material, a thermoelectric material, a magnetic material, a light-emitting material, a labeling agent, a ligand (e.g., a metal binding ligand), a nucleic acid, a polypeptide, a peptide, a biomineral, a polymer, an organic material, a therapeutically active agent (e.g., a drug) and an agent capable of modifying surface properties.

For example, the ordered structures may be in association with conducting or semiconducting materials, including, without limitation, inorganic structures such as Group IV, Group III/Group V, Group II/Group VI elements, transition group elements, or the like.

As used herein, the term "Group" is given its usual definition as understood by one of ordinary skill in the art. For instance, Group II elements include Zn, Cd and Hg; Group III elements include B, Al, Ga, In and Tl; Group IV elements include C, Si, Ge, Sn and Pb; Group V elements include N, P, As, Sb and Bi; and Group VI elements include O, S, Se, Te and Po.

Thus, for conducting materials, the ordered structures may enclose, or be in association with, for example, silver, gold, copper, platinum, nickel, or palladium. For semiconducting materials the ordered structures may enclose, for example, silicon, indium phosphide, gallium nitride and others.

In another example, the ordered structures may be attached to e.g., carbon nanotubes.

The ordered structures may also encapsulate, or be in association with, for example, any organic or inorganic molecules that are polarizable or have multiple charge states. For example, the ordered structures may include main group and metal atom-based wire-like silicon, transition metal-containing wires, gallium arsenide, gallium nitride, indium phosphide, germanium, or cadmium selenide structures.

Additionally, the ordered structure presented herein may enclose, or be in association with, various combinations of materials, including semiconductors and dopants. Representative examples include, without limitations, silicon, germanium, tin, selenium, tellurium, boron, diamond, or phosphorous. The dopant may also be a solid solution of various elemental semiconductors, for example, a mixture of boron and carbon, a mixture of boron and P, a mixture of boron and silicon, a mixture of silicon and carbon, a mixture of silicon and germanium, a mixture of silicon and tin, or a mixture of germanium and tin. In some embodiments, the dopant or the semiconductor may include mixtures of different groups, such as, but not limited to, a mixture of a Group III and a Group V element, a mixture of Group III and Group V elements, a mixture of Group II and Group VI semiconductors. Additionally, alloys of different groups of semiconductors may also be possible, for example, a combination of a Group II-Group VI and a Group III-Group V semiconductor and a Group I and a Group VII semiconductor.

The ordered structure presented herein may also enclose, or be in association with, a thermoelectric material that exhibits a predetermined thermoelectric power. Preferably, such a material is selected so that the resulting structure composition is characterized by a sufficient figure of merit. Such a composition may be used in thermoelectric systems and devices as heat transfer media or thermoelectric power sources. The thermoelectric material which can be encapsulated in, in association with, the structure of the present invention may be a bismuth-based material, such as, but not limited to, elemental bismuth, a bismuth alloy or a bismuth intermetallic compound. The thermoelectric material may also be a mixture of any of the above materials or other materials known to have thermoelectric properties. In addition the thermoelectric material may also include a dopant. Representative examples include, without limitation, bismuth telluride, bismuth selenide, bismuth antimony telluride, bismuth selenium telluride and the like.

The ordered structures presented herein may also enclose, or be in association with, magnetic materials. Generally, all materials in nature possess some kind of magnetic properties which are manifested by a force acting on a specific material when present in a magnetic field. These magnetic properties, which originate from the sub-atomic structure of the material, are different from one substrate to another. The direction as well as the magnitude of the magnetic force is different for different materials.

Whereas the direction of the force depends only on the internal structure of the material, the magnitude depends both on the internal structure as well as on the size (mass) of the material. The internal structure of the materials in nature, to which the magnetic characteristics of matter are related, is classified according to one of three major groups: diamagnetic, paramagnetic and ferromagnetic materials, where the strongest magnetic force acts on ferromagnetic materials.

In terms of direction, the magnetic force acting on a diamagnetic material is in opposite direction than that of the magnetic force acting on a paramagnetic or a ferromagnetic material. When placed in external magnetic field, a specific material acquires a non-zero magnetic moment per unit volume, also known as a magnetization, which is proportional to the magnetic field vector. For a sufficiently strong external magnetic field, a ferromagnetic material, due to intrinsic non-local ordering of the spins in the material, may retain its magnetization, hence to become a permanent magnet. As opposed to ferromagnetic materials, both diamagnetic and paramagnetic materials loose the magnetization once the external magnetic field is switched off.

Representative examples of paramagnetic materials which can be enclosed by, or be in association with, the ordered structure of the present embodiments include, without limitation, cobalt, copper, nickel, and platinum. Representative examples of ferromagnetic materials include, without limitation, magnetite and NdFeB.

Other materials which may be in association with the ordered structure of the present embodiments include, without limitation, light-emitting materials (e.g., dysprosium, europium, terbium, ruthenium, thulium, neodymium, erbium, ytterbium or any organic complex thereof), biominerals (e.g., calcium carbonate) and polymers (e.g., polyethylene, polystyrene, polyvinyl chloride, polynucleotides and polypeptides).

In some embodiments, the material associated with the ordered structure can be an active agent such as, for example, a surface active agent, a surface modifying agent, a bioactive agent, or can include two or more agents of any combination of the foregoing.

Agents that can be beneficially associated with the structures include, for example, therapeutically active agents, diagnostic agents, biological substances and labeling moieties. More particular examples include, but are not limited to, drugs, cells, proteins, enzymes, hormones, growth factors, nucleic acids, oligonucleotides, nucleic acid intercalators, antisense agents, organisms such as bacteria, fluorescence compounds or moieties, phosphorescence compounds or moieties, and radioactive compounds or moieties.

Surface active agents and surface modifying agents can be, for example, derived from chemical compounds that may modify surface properties of the structures. Such agents include, for example, surfactants, hydrophobic substances such as hydrocarbons being 4-30 carbon atoms in lengths, fatty acids or fatty acyls; carbohydrates; substituted or unsubstituted polyalkylene glycols (PEG), which, when substituted, can include one or more end groups such as, but not limited to, hydroxy, carboxy, alkoxy, amine, amide, hydrazine, thiol, azide, acetylene, acrylate, and any reactive/functional groups; maleimide and biotin/strepavidin.

In some embodiments, the agent is a bioactive agent, as described herein, and can be, for example, a diagnostic agent or a therapeutically active agent.

In some embodiments, the bioactive agent is a diagnostic agent.

As used herein, the phrase "diagnostic agent" describes an agent that upon administration to a body of a subject exhibits a detectable and/or measurable feature. These include, for example, labeling compounds or moieties, as is detailed hereinunder.

As used herein, the phrase "labeling compound or moiety" describes a detectable moiety or a probe which can be identified and traced by a detector using known techniques such as spectral measurements (e.g., fluorescence, phosphorescence), electron microscopy, X-ray diffraction and imaging, positron emission tomography (PET), single photon emission computed tomography (SPECT), magnetic resonance imaging (MRI), computed tomography (CT) and the like.

Representative examples of labeling compounds or moieties include, without limitation, chromophores, fluorescent agents, phosphorescent agents, contrast agents, radioactive agents, magnetic compounds or moieties (e.g., diamagnetic, paramagnetic and ferromagnetic materials), and heavy metal clusters, as is further detailed hereinbelow, as well as any other known detectable moieties.

The phrase "radioactive agent" describes a substance (i.e. radionuclide or radioisotope) which loses energy (decays) by emitting ionizing particles and radiation. When the substance decays, its presence can be determined by detecting the radiation emitted by it. For these purposes, a particularly useful type of radioactive decay is positron emission. Exemplary radioactive agents include $^{99m}Tc$ $^{18}F$ $^{131}I$ and $^{125}I$.

The term "magnetic agent" describes a substance which is attracted to an externally applied magnetic field. These substances are commonly used as contrast media in order to improve the visibility of internal body structures in Magnetic Resonance Imaging (MRI). The most commonly used compounds for contrast enhancement are gadolinium-based. MRI contrast agents alter the relaxation times of tissues and body cavities where they are present, which, depending on the image weighting, can give a higher or lower signal.

As used herein, the term "chromophore" describes a chemical moiety that, when attached to another molecule, renders the latter colored and thus visible when various spectrophotometric measurements are applied.

The term "bioluminescent agent" describes a substance which emits light by a biochemical process.

The term "chemiluminescent agent" describes a substance which emits light as the result of a chemical reaction.

The phrase "fluorescent agent" refers to a compound that emits light at a specific wavelength during exposure to radiation from an external source (excitation source).

The phrase "phosphorescent agent" refers to a compound emitting light without appreciable heat or external excitation as by slow oxidation of phosphorous.

A heavy metal cluster can be for example a cluster of gold atoms used, for example, for labeling in electron microscopy techniques.

In some embodiments, the bioactive agent is a targeting agent or moiety.

As used herein and in the art, the phrase "targeting agent or moiety" describes a chemical entity which has an affinity to a bodily site such as, for example, to organs or tissues overexpressing a biomolecule (e.g., receptor, enzyme, hormone), or to organs or tissues which are enriched with a chemical or biological moiety (e.g., hydroxyapetite in bone tissues). A targeting moiety can be, for example, a receptor ligand, an enzyme substrate, a bone targeting moiety, a moiety that enhances blood-brain barrier permeability, antibodies or fragments thereof, including monoclonal antibodies, lipoproteins, hormones and artificial analogs thereof, charged molecules, polysaccharides, peptides, nucleic acids (aptamers), small molecules such as, for example, folic acid, biotin, bisphosphonate, vitamins, avidin and/or strepavidin.

In some embodiments, the bioactive agent is a therapeutically active agent.

As used herein, the phrase "therapeutically active agent" describes a chemical substance, which exhibits a therapeutic activity when administered to a subject. These include, as non-limiting examples, inhibitors, ligands (e.g., receptor agonists or antagonists), co-factors, anti-inflammatory drugs (steroidal and non-steroidal), anti-psychotic agents, analgesics, anti-thrombogenic agents, anti-platelet agents, anti-coagulants, anti-diabetics, statins, toxins, antimicrobial agents, anti-histamines, metabolites, anti-metabolic agents, vasoactive agents, vasodilator agents, cardiovascular agents, chemotherapeutic agents, antioxidants, phospholipids, anti-proliferative agents and heparins.

The therapeutically active agent can be a small molecule or a biological substance.

As used herein, the phrase "biological substance" refers to a substance that is present in, or is derived from, a living organism or cell tissue. This phrase also encompasses the organisms, cells and tissues. Representative examples therefore include, without limitation, cells, amino acids, peptides, proteins, oligonucleotides, nucleic acids, nucleic acid intercalators, genes, hormones, growth factors, enzymes, co-factors, antisenses, antibodies, antigens, vitamins, immunoglobulins, cytokines, prostaglandins, vitamins, toxins and the like, as well as organisms such as bacteria, viruses, fungi and the like.

Therapeutically active agents that are suitable for use in the context of some embodiments of the present invention can be small molecules or biomolecules, including, without limitation, anti-proliferative agents, chemotherapeutic agents, radiopharmaceuticals, steroids, vitamins, angiogenesis-promoters, angiogenesis inhibitors, drugs, anti-histamines, antimicrobial agents, antidepressants, anti-psychotic agents, anti-hypertensive agents, anti-inflammatory agents, antioxidants, anti-viral agents, anasthial agents, co-factors, cholesterol, fatty acids, bile acids, saponins, hormones, inhibitors, ligands; cytokines, chemokines, chemo-attractants, chemo-repellants, agonists, antagonists, antibodies, antigens, enzymes, co-factors, growth factors, haptens, hormones, and toxins; nucleotide-based substances such as DNA, RNA, oligonucleotides, labeled oligonucleotides, nucleic acid constructs, and antisenses; saccharides, polysaccharides, phospholipids, glycolipids, viruses and cells.

Some bioactive agents which can be beneficially associated with the structures or composition-of-matter include genetic therapeutic agents and proteins, such as ribozymes, anti-sense polynucleotides and polynucleotides coding for a specific product (including recombinant nucleic acids) such as genomic DNA, cDNA, or RNA. The polynucleotide can be provided in "naked" form or in connection with vector systems that enhances uptake and expression of polynucleotides. These can include DNA compacting agents (such as histones), non-infectious vectors (such as plasmids, lipids, liposomes, cationic polymers and cationic lipids) and viral vectors such as viruses and virus-like particles (i.e., synthetic particles made to act like viruses). The vector may further have attached peptide targeting sequences, anti-sense nucleic acids (DNA and RNA), and DNA chimeras which include gene sequences encoding for ferry proteins such as membrane translocating sequences ("MTS"), tRNA or rRNA to replace defective or deficient endogenous molecules and herpes simplex virus-1 ("VP22").

Additional bioactive agents which can be beneficially associated with the structures or composition-of-matter include gene delivery agents, which may be either endogenously or exogenously controlled. Examples of endogenous control include promoters that are sensitive to a physiological signal such as hypoxia or glucose elevation. Exogenous control systems involve gene expression controlled by administering a small molecule drug. Examples include tetracycline, doxycycline, ecdysone and its analogs, RU486, chemical dimerizers such as rapamycin and its analogs, etc.

Additional bioactive agents which can be beneficially associated with the structures or composition-of-matter include viral and non-viral vectors, such as adenoviruses, gutted adenoviruses, adeno-associated virus, retroviruses, alpha virus (Semliki Forest, Sindbis, etc.), lentiviruses, herpes simplex virus, ex vivo modified cells (i.e., stem cells, fibroblasts, myoblasts, satellite cells, pericytes, cardiomyocytes, skeletal myocytes, macrophage, etc.), replication competent viruses (ONYX-015, etc.), and hybrid vectors, artificial chromosomes and mini-chromosomes, plasmid DNA vectors (pCOR), cationic polymers (polyethyleneimine, polyethyleneimine (PEI) graft copolymers such as polyether-PEI and polyethylene oxide-PEI, neutral polymers PVP, SP1017 (SUPRATEK), lipids or lipoplexes, nanoparticles and microparticles with and without targeting sequences such as the protein transduction domain (PTD).

Any of the active agents described herein can be associated with (e.g., attached to) the structures or composition-of-matter via biostable or biocleavable interactions.

For example, diagnostic agents and targeting agents or moieties can be attached to the structures or composition-of-matter by biostable interactions (e.g., biostable chemical bonds), whereby therapeutically active agents can be attached to the structures or composition-of-matter via biocleavable bonds or linking moieties, as defined hereinafter.

Any of the compositions as described herein can be used as a part of, or in manufacturing, articles-of-manufacturing or devices.

Exemplary such article-of-manufacture or devices include, but are not limited to, a medicament or drug-delivery system (e.g., for releasing the polypeptide, biomineral or therapeutically active agent), a nucleic acid probe, a biosensor, an electrical device, a semiconducting article or device, a thermoelectric article or device, a magnetic article, a light-emitting article or device, a polymeric article, a metallic article or device, and an article or device having activated surface.

The PNA monomer-based self-assembled structures described herein may serve in a variety of technological applications in fields such as material science, spectroscopy and bionanotechnology.

Photonic Crystal:

In the course of studying the self-assembly of PNA monomers as described herein, the present inventors have uncovered that upon formation of the ordered structures from the plurality of PNA monomers as described herein, at least a portion of these structures further arrange so as to form an ordered array of these structures that features a crystalline structure, that is, the structures are periodically arranged as in a crystalline lattice.

The present inventors have further uncovered that the ordered array of these structures acts as a photonic crystal, such that the structures are periodically arranged so as to exhibit a periodic modulation in a refractive index thereof.

The present inventors have further uncovered that the photonic crystal is a tunable photonic crystal, as defined herein.

As discussed in the background section hereinabove, photonic structures that are found in nature are often made of guanine building blocks, exploiting the very high refractive index of guanine crystals.

Previous attempts to produce guanine-based photonic crystals were found unsuccessful. The production of artificial guanine-based photonic crystals has therefore never been described hitherto.

According to an aspect of some embodiments of the present invention, there is provided an artificial photonic crystal which comprises a plurality of guanine-containing ordered structures periodically arranged. In some embodiments, the structures are periodically arranged so as to exhibit a periodic modulation in a refractive index thereof.

By "artificial" it is meant a photonic crystal that is not found in nature and which is made of synthetic building blocks (e.g., building blocks that are not naturally-occurring and/or are not originating (e.g., extracted) from a natural source).

According to an aspect of some embodiments of the present invention, there is provided an artificial photonic crystal comprising a plurality of guanine-containing ordered structures periodically arranged, and which is tunable, as defined herein, in response to a change in osmolarity of a solution (e.g., aqueous solution) contacting the photonic crystal, as defined hereinbelow.

The guanine-containing ordered structures are, in some embodiments, structures made of a plurality of modified guanine-containing compounds which self-assemble into the ordered structures.

In some embodiments, the guanine-containing compounds are monomeric compounds, that is, they do not form a part of oligomeric or polymeric nucleic acids or analogs thereof, for example, peptide nucleic acid oligomers or polymers.

The guanine-containing compounds, in some embodiments, comprise one or more aromatic moieties, as defined herein, attached thereto.

In some embodiments, the guanine-containing compounds forming the ordered structures are guanine analogs, such as, for example, represented by Formula III hereinabove, in which an aromatic moiety is attached either to the amine group (as $R_{20}$) and/or as a substituent to any other position of the guanine.

In some embodiments, at least one aromatic moiety is attached to the amine group of the guanine.

In some other embodiments, the guanine-containing compound is an N-protected guanine, in which the amine group of the guanine is capped by an N-protecting moiety, as described herein.

In some of these embodiments, the N-protecting moiety is an aromatic N-protecting moiety as defined herein.

In some embodiments, the guanine-containing compound is a guanine-based PNA monomer, and in some embodiments, it is a guanine-based modified PNA monomer as described in any of the embodiments described herein, and any combination thereof.

According to an aspect of some embodiments of the present invention there is provided a photonic crystal comprising a plurality of ordered structures formed of, or composed of, PNA monomers as described herein, the structures being periodically arranged to form the crystal.

Herein throughout, the phrase "periodically arranged" means that the PNA monomer-based ordered structures form a periodic array, which is a repeated structure with a substantially similar size and/or spacing along at least one dimension. For example, structures in a two dimensional periodic array may have a first spacing in a first direction and different spacing in another direction. In general, for a three dimensional photonic crystal, the x, y, and z periodicities can be different.

In some embodiments, the plurality of structures are periodically arranged so as to exhibit a periodic modulation in a refractive index thereof.

Herein throughout, the phrase "periodic modulation in a refractive index" means that the crystal exhibits different values of refractive indices, and that the crystal is arranged such that the variability in refractive indices is periodic. This phrase means that the refractive index varies in the same manner over each of a plurality of spatial regions adjacent to each other. Preferably, each of the spatial regions having a size (e.g., length, when the regions are one-dimensional, diameter or area when the regions are two-dimensional) referred to herein as a "period" of the modulation. The variation of the refractive index within the regions is preferably such that the value of the refractive index has the same spatial dependence within any two adjacent spatial regions.

Typically, the refractive index has at least 2 or at least 3 or at least 4 or at least 5 or at least 6 or at least 7 or at least 8 or at least 9 or at least 10 different values within each region, wherein each such value is within a refractive index interval of from about 1.5 to about 2, or from about 1.5 to about 1.85, or from about 1.5 to about 1.8, including any subranges and intermediate values therebetween.

In some embodiments, the structures are arranged to form a two-dimensional ordered array. In some embodiments, the array features a hexagonal symmetry arrangement. Any other 2-dimensional arrangements of a periodic array are contemplated.

In some embodiments, the periodic modulation of refractive indices arises from a two-dimensional ordered array, as described herein. That is, the periodic modulation is in two dimensions. In such a structure there is a reflectance peak for incident light in two directions—along the plane of the repeating units in the periodic array forming the crystal.

In some of any of the embodiments described herein for a photonic crystal, the crystal is characterized by a reflectance wavelength range.

The wavelength reflected by a photonic crystal is dependent on the periodic structural modulation of the refractive index.

In some embodiments, the reflectance wavelength range of a photonic crystal as described herein spans from about 400 nm to about 650 nm.

In some embodiments, a photonic crystal as described herein is a tunable photonic crystal.

A photonic crystal is considered "tunable" when the wavelength or range of wavelengths reflected by the crystal may be shifted in response to an external stimulus.

Typically, the wavelength reflected by a photonic crystal may be shifted by changes in the photonic crystal structure (e.g., the lattice spacing), in the refractive index, or in any other or all components of the photonic crystal.

In some embodiments, the periodic modulation of refractive indices is responsive to an external stimulus.

In some embodiments, the reflectance wavelength range of the photonic crystal is shifted in response to the external stimulus. In some embodiments, a shift in the reflectance wavelength range is of from 10 nm to 600 nm, including any subranges and intermediate values therebetween.

The external stimulus can be chemical, physical or mechanical.

For example, a chemical external stimulus may be a change in the chemical properties of an environment of the photonic crystal, which results in a structural change of the crystal and hence in a change in the reflectance wavelength range.

By "environment" it means a medium (liquid, solid and/or gas) that is in contact with the photonic crystal in a proximity sufficient to induce a structural change in the crystal.

A chemical or physical change in the environment may affect, for example, the distance between the structures in the periodic array, due to a change in intermolecular interactions between the structures.

A chemical or physical change in the environment can otherwise affect a refractive index in the crystal and thus may affect the periodic modulation of refractive indices.

A mechanical change in the environment typically changes the spatial distance between the structures forming the crystal.

Chemical external stimuli include, for example, a change in osmolarity, a change in a dielectric constant, addition of molecules that can interact with the structures forming the crystals to thereby affect the intermolecular interactions between the structures (e.g., oligonucleotides, polynucleotides, nucleobase, DNA binding small molecules, metal ions etc.).

In some embodiments, the photonic crystal is responsive to a chemical external stimulus which is a change in the osmolarity of a solution that contacts the crystal.

In some embodiments, the photonic crystal is in contact with the liquid/air interface of an aqueous solution, and a change in the reflectance wavelength range of the crystal is effected by a change in the osmolarity of the solution.

By "osmolarity" it is meant herein a concentration of a solute in a solution. A change in osmolarity therefore encompasses, for example, any addition of a water-soluble material to water or an aqueous solution, which thus changes the concentrations of solutes in an aqueous solution and hence the osmolarity of the solution.

In some embodiments, a change in the osmolarity of a solution is effected by a change in the salt concentration in an aqueous solution (e.g., by addition of salt to an aqueous solution contacting the photonic crystal). The external stimulus in such a case is an addition of salt to the aqueous solution.

Preferably, the salt is a water-soluble salt, and the aqueous solution comprises water. An additional of a water-soluble salt to water substantially changes the solution osmolarity.

In some embodiments, the photonic crystal is responsive to an external stimulus which is a change in a dielectric constant of a solution contacting the photonic crystal. Such a change can be effected chemically, for example, by introducing to an aqueous solution contacting the crystal a water-miscible polar solvent. Such a change can otherwise be effected physically, for example, by application of electric field to an aqueous solution contacting the crystal.

Alternatively, a photonic crystal can be deposited on an electrode, and voltage is applied. This is induced an electrical external stimulus.

A mechanical external stimulus can be induced, for example, by mechanical deformation of a solid or semi-solid matrix on or in which the crystal is deposited. Exemplary such matrices include, for example, flexible matrices such as elastomers, hydrogels, etc.

Examples of controlling reflectance wavelengths of photonic crystals are described in U.S. Patent Application Publication No. 2004/0131799, PCT Application Publication No. WO 2008/098339, and U.S. Patent Application Publication No. 2009/0034051. Deformable photonic crystals non-close-packed spheres embedded in an hydrogel or elastomer matrix, for example, are discussed in U.S. Pat. Nos. 6,544,800, 5,266,238 and 5,368,781, Holtz et al. in Nature 389:829-832, Foulger et al. in Advanced Materials 13:1898-1901, Asher et al. in Journal of the Material Chemical Society 116:4997-4998, and Jethmalani et al. in Chemical Materials 8:2138-2146, all of which are incorporated by reference as if fully set forth herein.

Also provided according to some embodiments of the present invention are methods of tuning or controlling a reflectance wavelength range of a photonic crystal as described herein, which are effected by subjecting the crystal to an external stimulus, as described herein.

In some embodiments, a method is effected by changing an osmolarity of an aqueous solution contacting the photonic crystal, as described herein.

Also provided according to some embodiments of the present invention are processes of preparing a photonic crystal as described herein, for example, a guanine-based artificial photonic crystal or a photonic crystal made of PNA monomer-based structures as described herein.

A process, according to some of these embodiments, is effected by generating ordered structures as described herein in any of the respective embodiments preferably by contacting the respective monomers (e.g., a plurality of PNA monomers as described herein, or, alternatively, guanine-containing building blocks) with an aqueous solution, preferably in water, as described herein.

In some embodiments, the volume of the aqueous solution is at least 5 ml, or at least 10 ml, or at least 20 ml.

In some embodiments, the contacting is effected such that a surface area of a solution/air interface is at least 1 $cm^2$, or at least 2, 3, 4, 5 or 10 $cm^2$, while higher surface areas of the interface are also contemplated.

As demonstrated herein, PNA monomers as described herein self assemble into ordered structures upon being contacted with an aqueous solution, and at suitable solution volume and/or surface area of a solution/air interface, some of these structures further arrange to form a photonic crystal as described herein.

In some embodiments, the process therefore further comprises allowing at least a portion of the ordered structures to arrange so as to form a photonic crystal.

In some embodiments, the process further comprises isolating the photonic crystal.

Isolation of the photonic crystal can be effected, for example, by decanting the aqueous solution, by withdrawing the aqueous solution by means of, for example, syringe or pump, or by otherwise separating the crystal from the aqueous solution, and optionally drying the crystal.

In some embodiments, the process further comprises depositing the photonic crystal on a solid substrate (e.g., a glass substrate or any other solid matrix).

The deposition can be made by placing the substrate in a reaction vessel and withdrawing the aqueous solution once the crystal is formed, to thereby have the crystal deposited in the substrate. Other deposition techniques known in the art are also contemplated.

The photonic crystals provided herewith can be utilized in various technologies and applications in which photonic crystals, and particularly tunable photonic crystals can be advantageously used.

These include, for example, various spectroscopic applications such as optical sensors, spectroscopic devices and methodologies based on diffraction gratings, spectroscopic devices and methodologies based on surface enhances Raman spectroscopy (SERS), optical transistors, optical fibers and optical coatings.

Tunable photonic crystals can be further used as sensors, indicators, and for authentication, or display applications.

Tunable photonic crystals can be further used, for example, in paints, inks, pigments and like incorporating the photonic crystals. Paints and inks containing tunable photonic crystals provide color-changing paints and inks (which can, for example, change color in response to a stimulus like electric stimulus, or thermal stimulus).

Tunable photonic crystals can be further used to make up cosmetic formulations such as creams, make-ups, lipsticks, lacquers, eye-shadows, lotions, sunscreen formulations, and any other cosmetic formulation that can benefit from the opalescent effect of the crystals, in addition to its biocompatibility.

Tunable photonic crystals can be further used in fibers, for producing, for example, opalescent fabrics, or, when the photonic crystal is tunable, color changing fabrics or other fibrillar materials. The photonic crystals can be dispersed in or attached to a polymeric material used to form the fiber or fabric.

According to an aspect of some embodiments of the present invention there are provided articles-of-manufacturing comprising a photonic crystal as described herein.

Depending on the selected article and its intended use, the photonic crystals in the article can be deposited on a solid matrix, embedded within a solid matrix, or dispersed or suspended in a formulation.

Exemplary non-limiting articles include optical devices useful as sensors, indicators and in authentication and display applications; devices, apparatuses and systems useful in spectroscopic applications as described herein (e.g., SERS); ink formulations, paint formulations, pigment formulations, incorporating the photonic crystals, optionally coated by an optical coating; fibers, fabrics and other polymeric materials incorporating the photonic crystal; and cosmetic formulations as described herein, incorporating the photonic crystals, optionally within the base carrier.

General:

It is expected that during the life of a patent maturing from this application many relevant modified PNA and/or nucleobase analogs will be developed and the scope of the terms "PNA monomer", "modified PNA monomer", "nucleobase" and "nucleobase analog" is intended to include all such new technologies a priori.

As used herein the term "about" refers to ±10% or ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" or "process" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Chemical:

As used herein, the term "amine" describes both a —NR'R" group and a —NR'— group, wherein R' and R" are each independently hydrogen, alkyl, cycloalkyl, aryl, as these terms are defined hereinbelow.

The amine group can therefore be a primary amine, where both R' and R" are hydrogen, a secondary amine, where R' is hydrogen and R" is alkyl, cycloalkyl or aryl, or a tertiary amine, where each of R' and R" is independently alkyl, cycloalkyl or aryl.

Alternatively, R' and R" can each independently be hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, carbonyl, C-carboxylate, O-carboxylate, N-thiocarbamate, O-thiocarbamate, urea, thiourea, N-carbamate, O-carbamate, C-amide, N-amide, guanyl, guanidine and hydrazine, as these terms are defined herein.

The term "amine" is used herein to describe a —NR'R" group in cases where the amine is an end group, as defined hereinunder, and is used herein to describe a —NR'— group in cases where the amine is a linking group.

Herein throughout, the phrase "end group" describes a group (a substituent) that is attached to another moiety in the compound via one atom thereof.

The phrase "linking group" describes a group (a substituent) that is attached to another moiety in the compound via two or more atoms thereof.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 carbon atoms. Most preferably, unless otherwise indicated, the alkyl is a lower alkyl having 1 to 4 carbon atoms. The alkyl group may be substituted or unsubstituted. Substituted alkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

The alkyl group can be an end group, as this phrase is defined hereinabove, wherein it is attached to a single adjacent atom, or a linking group, as this phrase is defined hereinabove, which connects two or more moieties via at least two carbons in its chain. When the alkyl in a linking group, it is also referred to herein as "alkylene".

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted. Substituted cycloalkyl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The cycloalkyl group can be an end group, as this phrase is defined hereinabove, wherein it is attached to a single adjacent atom, or a linking group, as this phrase is defined hereinabove, connecting two or more moieties at two or more positions thereof.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted. Substituted aryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine. The aryl group can be an end group, as this term is defined hereinabove, wherein it is attached to a single adjacent atom, or a linking group, as this term is defined hereinabove, connecting two or more moieties at two or more positions thereof.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline and purine. The heteroaryl group may be substituted or unsubstituted. Substituted heteroaryl may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroaryl group can be an end group, as this phrase is defined hereinabove, where it is attached to a single adjacent atom, or a linking group, as this phrase is defined hereinabove, connecting two or more moieties at two or more positions thereof. Representative examples are pyridine, pyrrole, oxazole, indole, purine and the like.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Substituted heteroalicyclic may have one or more substituents, whereby each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, O-carbamate, N-carbamate, C-amide, N-amide, guanyl, guanidine and hydrazine. The heteroalicyclic group can be an end group, as this phrase is defined hereinabove, where it is attached to a single adjacent atom, or a linking group, as this phrase is defined hereinabove, connecting two or more moieties at two or more positions thereof. Representative examples are piperidine, piperazine, tetrahydrofuran, tetrahydropyrane, morpholino and the like.

The term "halide" and "halo" describes fluorine, chlorine, bromine or iodine.

The term "haloalkyl" describes an alkyl group as defined above, further substituted by one or more halide.

The term "sulfate" describes a —O—S(=O)$_2$—OR' end group, as this term is defined hereinabove, or an —O—S(=O)$_2$—O— linking group, as these phrases are defined hereinabove, where R' is as defined hereinabove.

The term "thiosulfate" describes a —O—S(=S)(=O)—OR' end group or a —O—S(=S)(=O)—O— linking group, as these phrases are defined hereinabove, where R' is as defined hereinabove.

The term "sulfite" describes an —O—S(=O)—O—R' end group or a —O—S(=O)—O— group linking group, as these phrases are defined hereinabove, where R' is as defined hereinabove.

The term "thiosulfite" describes a —O—S(=S)—O—R' end group or an —O—S(=S)—O— group linking group, as these phrases are defined hereinabove, where R' is as defined hereinabove.

The term "sulfinate" describes a —S(=O)—OR' end group or an —S(=O)—O— group linking group, as these phrases are defined hereinabove, where R' is as defined hereinabove.

The term "sulfoxide" or "sulfinyl" describes a —S(=O)R' end group or an —S(=O)— linking group, as these phrases are defined hereinabove, where R' is as defined hereinabove.

The term "sulfonate" describes a —S(=O)$_2$—R' end group or an —S(=O)$_2$— linking group, as these phrases are defined hereinabove, where R' is as defined herein.

The term "S-sulfonamide" describes a —S(=O)$_2$—NR'R" end group or a —S(=O)$_2$—NR'— linking group, as these phrases are defined hereinabove, with R' and R" as defined herein.

The term "N-sulfonamide" describes an R'S(=O)$_2$—NR"— end group or a —S(=O)$_2$—NR'— linking group, as these phrases are defined hereinabove, where R' and R" are as defined herein.

The term "disulfide" refers to a —S—SR' end group or a —S—S— linking group, as these phrases are defined hereinabove, where R' is as defined herein.

The term "phosphonate" describes a —P(=O)(OR')(OR") end group or a —P(=O)(OR')(O)— linking group, as these phrases are defined hereinabove, with R' and R" as defined herein.

The term "thiophosphonate" describes a —P(=S)(OR')(OR") end group or a —P(=S)(OR')(O)— linking group, as these phrases are defined hereinabove, with R' and R" as defined herein.

The term "phosphinyl" describes a —PR'R" end group or a —PR'— linking group, as these phrases are defined hereinabove, with R' and R" as defined hereinabove.

The term "phosphine oxide" describes a —P(=O)(R')(R") end group or a —P(=O)(R')— linking group, as these phrases are defined hereinabove, with R' and R" as defined herein.

The term "phosphine sulfide" describes a —P(=S)(R')(R") end group or a —P(=S)(R')— linking group, as these phrases are defined hereinabove, with R' and R" as defined herein.

The term "phosphite" describes an —O—PR'(=O)(OR") end group or an —O—PH(=O)(O)— linking group, as these phrases are defined hereinabove, with R' and R" as defined herein.

The term "oxime" describes a =N—OH end group or a =N—O— linking group, as these phrases are defined hereinabove.

The term "hydroxyl" describes a —OH group.

The term "alkoxy" describes both an —O-alkyl and an —O-cycloalkyl group, as defined herein.

The term "aryloxy" describes both an —O-aryl and an —O-heteroaryl group, as defined herein.

The term "thiohydroxy" or "thiol" describes a —SH group.

The term "thioalkoxy" describes both a —S-alkyl group, and a —S-cycloalkyl group, as defined herein.

The term "thioaryloxy" describes both a —S-aryl and a —S-heteroaryl group, as defined herein.

The term "cyano" describes a —C≡N group.

The term "isocyanate" describes an —N=C=O group.

The term "nitro" describes an —NO$_2$ group.

The term "acyl halide" describes a —(C=O)R'''' group wherein R'''' is halide, as defined hereinabove.

The term "azo" or "diazo" describes an —N=NR' end group or an —N=N— linking group, as these phrases are defined hereinabove, with R' as defined hereinabove.

The term "peroxo" describes an —O—OR' end group or an —O—O— linking group, as these phrases are defined hereinabove, with R' as defined hereinabove.

The term "carbonyl" or "carbonate" as used herein, describes a —C(=O)—R' end group or a —C(=O)— linking group, as these phrases are defined hereinabove, with R' as defined herein.

The term "thiocarbonyl" as used herein, describes a —C(=S)—R' end group or a —C(=S)— linking group, as these phrases are defined hereinabove, with R' as defined herein.

The term "carboxy" as used herein in some embodiments encompasses groups that comprise a —C(=O)— moiety, and hence generally describes carboxylates, including C-carboxylate and O-carboxylate; thiocarboxylates, amides, carbamates, thiocarbamates, urea, guanyl, guanidyl, and the like.

The term "C-carboxylate" describes a —C(=O)—OR' end group or a —C(=O)—O— linking group, as these phrases are defined hereinabove, where R' is as defined herein.

The term "O-carboxylate" describes a —OC(=O)R' end group or a —OC(=O)— linking group, as these phrases are defined hereinabove, where R' is as defined herein.

The term "C-thiocarboxylate" describes a —C(=S)—OR' end group or a —C(=S)—O— linking group, as these phrases are defined hereinabove, where R' is as defined herein.

The term "O-thiocarboxylate" describes a —OC(=S)R' end group or a —OC(=S)— linking group, as these phrases are defined hereinabove, where R' is as defined herein.

The term "N-carbamate" describes an R"OC(=O)—NR'— end group or a —OC(=O)—NR'— linking group, as these phrases are defined hereinabove, with R' and R" as defined herein.

The term "O-carbamate" describes an —OC(=O)—NR'R" end group or an —OC(=O)—NR'— linking group, as these phrases are defined hereinabove, with R' and R" as defined herein.

The term "O-thiocarbamate" describes a —OC(=S)—NR'R" end group or a —OC(=S)—NR'— linking group, as these phrases are defined hereinabove, with R' and R" as defined herein.

The term "N-thiocarbamate" describes an R"OC(=S)NR'— end group or a —OC(=S)NR'— linking group, as these phrases are defined hereinabove, with R' and R" as defined herein.

The term "S-dithiocarbamate" describes a —SC(=S)—NR'R" end group or a —SC(=S)NR'— linking group, as these phrases are defined hereinabove, with R' and R" as defined herein.

The term "N-dithiocarbamate" describes an R"SC(=S)NR'— end group or a —SC(=S)NR'— linking group, as these phrases are defined hereinabove, with R' and R" as defined herein.

The term "urea", which is also referred to herein as "ureido", describes a —NR'C(=O)—NR"R'" end group or a —NR'C(=O)—NR"— linking group, as these phrases are defined hereinabove, where R' and R" are as defined herein and R'" is as defined herein for R' and R".

The term "thiourea", which is also referred to herein as "thioureido", describes a —NR'—C(=S)—NR"R'" end group or a —NR'—C(=S)—NR"— linking group, with R', R" and R'" as defined herein.

The term "C-amide" describes a —C(=O)—NR'R" end group or a —C(=O)—NR'— linking group, as these phrases are defined hereinabove, where R' and R" are as defined herein.

The term "N-amide" describes a R'C(=O)—NR"— end group or a R'C(=O)—N— linking group, as these phrases are defined hereinabove, where R' and R" are as defined herein.

The term "guanyl" describes a R'R"NC(=N)— end group or a —R'NC(=N)— linking group, as these phrases are defined hereinabove, where R' and R" are as defined herein.

The term "guanidyl" describes a —R'NC(=N)—NR"R'" end group or a —R'NC(=N)—NR"— linking group, as these phrases are defined hereinabove, where R', R" and R'" are as defined herein.

The term "hydrazine" describes a —NR'—NR"R'" end group or a —NR'—NR"— linking group, as these phrases are defined hereinabove, with R', R", and R'" as defined herein.

As used herein, the term "hydrazide" describes a —C(=O)—NR'—NR"R'" end group or a —C(=O)—NR'—NR"— linking group, as these phrases are defined hereinabove, where R', R" and R'" are as defined herein.

As used herein, the term "thiohydrazide" describes a —C(=S)—NR'—NR"R'" end group or a —C(=S)—NR'—NR"— linking group, as these phrases are defined hereinabove, where R', R" and R'" are as defined herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Self-Assembled PNA Nanostructures

Pna Monomers:

The following PNA monomers (building blocks) were tested:

Guanine PNA monomer of the formula:

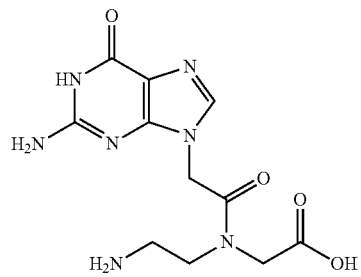 [SMILES: NCCN(CC(=O)O)C(=O)Cn1cnc2c(=O)[nH]c(N)nc21]

Fmoc-protected Guanine PNA monomer (also referred to herein as single-protected Guanine) of the formula:

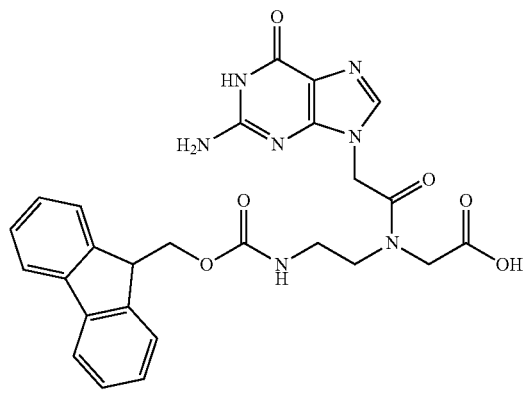 [SMILES: Nc1nc2c(ncn2CC(=O)N(CCNC(=O)OCC2c3ccccc3-c3ccccc32)CC(=O)O)c(=O)[nH]1]

Fmoc, Bhoc-protected Guanine PNA monomer (also referred to herein as Fmoc-G-Bhoc; N—(N-Fmoc-2-amino-ethyl)-N—[(N-6-Bhoc-9-guanyl)acetyl]-glycine; Fmoc-G-(Bhoc)-aeg-OH; or double-protected Guanine monomer) of the formula:

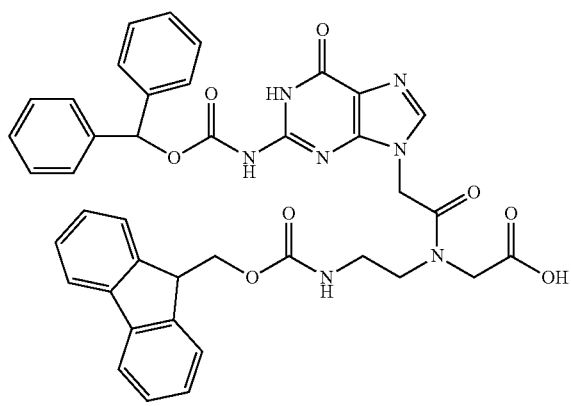 [SMILES: O=C(O)CN(CCNC(=O)OCC1c2ccccc2-c2ccccc21)C(=O)Cn1cnc2c(=O)[nH]c(NC(=O)OC(c3ccccc3)c3ccccc3)nc21]

Adenine PNA monomer of the formula:

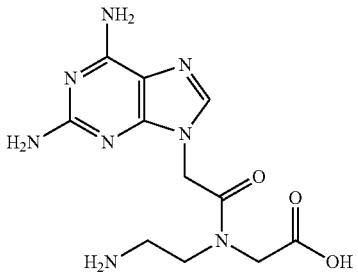 [SMILES: NCCN(CC(=O)O)C(=O)Cn1cnc2c(N)nc(N)nc21]

Fmoc-protected Adenine PNA monomer (also referred to herein as single-protected Adenine) of the formula:

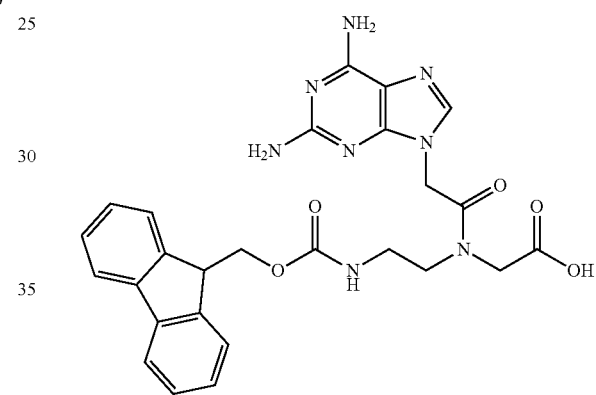

Fmoc, Bhoc-protected Adenine PNA monomer (also referred to herein as Fmoc-A-Bhoc; or Fmoc-A-(Bhoc)-aeg-OH; or double-protected Adenine) of the formula:

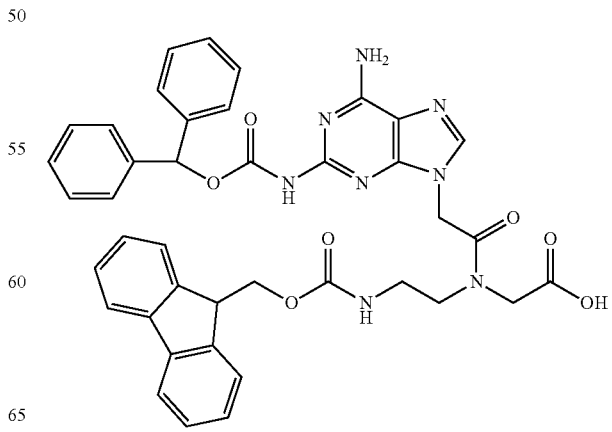

Cytosine PNA monomer of the formula:

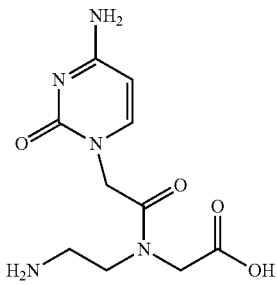 [SMILES: NCCN(CC(=O)O)C(=O)Cn1ccc(N)nc1=O]

Fmoc-protected Cytosine PNA monomer (also referred to herein as single-protected Cytosine) of the formula:

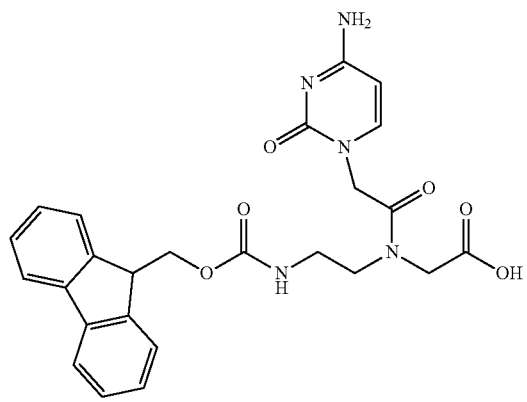 [SMILES: Nc1ccn(CC(=O)N(CCNC(=O)OCC2c3ccccc3-c3ccccc32)CC(=O)O)c(=O)n1]

Fmoc, Bhoc-protected Cytosine PNA monomer (also referred to herein as Fmoc-C-Bhoc; or Fmoc-C-(Bhoc)-aeg-OH; or double-protected Cytosine) of the formula:

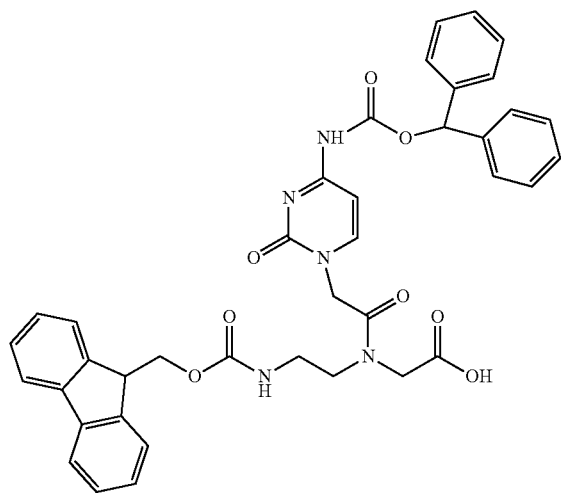 [SMILES: O=C(O)CN(CCNC(=O)OCC1c2ccccc2-c2ccccc21)C(=O)Cn1ccc(NC(=O)OC(c2ccccc2)c2ccccc2)nc1=O]

Thymine PNA monomer of the formula:

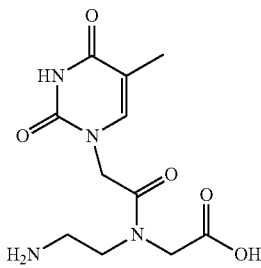 [SMILES: Cc1cn(CC(=O)N(CCN)CC(=O)O)c(=O)[nH]c1=O]

Fmoc-protected Thymine PNA monomer (also referred to herein as Fmoc-T) of the formula:

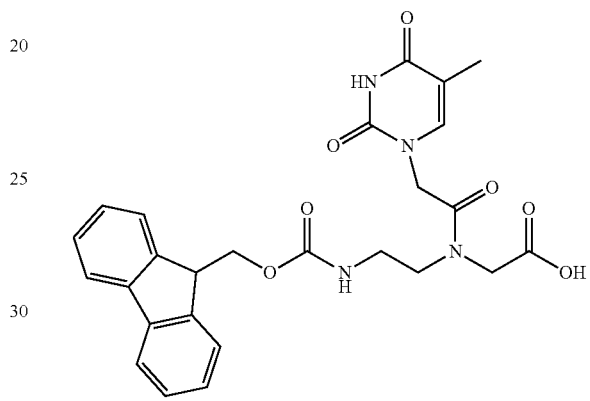

The Fmoc, Bhoc-protected (double-protected) Guanine, Adenine and Cytosine PNA monomers are commercially available building blocks for solid phase synthesis of PNA oligomers, and were obtained from PolyOrg Inc.

Fmoc-protected (single-protected) PNA monomers of Guanine, Adenine and Cytosine were obtained by selectively removing the Bhoc-protecting group. Briefly, solid-phase PNA synthesis (0.1 mmol scale) was manually carried out using either Fmoc-PAL-PEG-PS resin (0.10 mmol/gr) or NovaPEG Rink Amide resin (0.45 mmol/gr). The resin was weighted and stirred in a swelling solution containing DMF (dimethylformamide) and DCM (dichloromethane) at a 1:1 volume ratio for 2 hours. The resin was thereafter treated a cleavage solution for removing the Fmoc protecting-group at the amino-terminus, by mixing with a solution containing 20% piperidine in DMF for 15 minutes, twice. Then, the double protected Bhoc,Fmoc-PNA monomer was introduced to the resin by using a pre-activation solution (HBTU, HOBT, and DIEA in DMF) of the relevant monomer. The resin was stirred with the monomer solution for 2-3 hours.

The obtained resin (having the double-protected PNA monomer conjugated thereto) was thereafter washed repeatedly with DCM (dichloromethane) and methanol, dried under vacuum, and then treated with a cleavage solution (1 ml per 100 mg) selective for removing the Bhoc protecting group and for cleaving the monomer from the resin, containing 90% TFA (trifluoroacetic acid) and 10% m-cresol for 10 minutes on ice and then stirred for 90 minutes at room temperature. Following the TFA was evaporated under nitrogen stream and the free peptide was precipitated by 30 ml of cold ether. The supernatant was removed using centrifugation at 3000 rpm for 5 minutes. Following 2 additional cycles of precipitation in cold ether and centrifugation, the precipitate was dried under vacuum.

The resulting crude PNA was analyzed by analytical HPLC which usually showed about 95% purity and was used without further purification. When necessary, the crude product was purified by reversed-phase high-performance liquid chromatography using a $C_8$ column. The fractions corresponding to the desired product were collected and lyophilized to afford an off-white powder. The product was verified by electrospray ionization time-of-flight mass spectrometry.

The non-protected PNA monomers were prepared by using the same procedure as described hereinabove, for preparing a single-protected PNA monomer, while reacting the bound monomer, before its cleavage from the resin, with a solution of 20% piperidine in DMF for 15 minutes, twice, for removing the Fmoc protecting group.

Fmoc-protected Thymine PNA monomer was purchased from PolyOrg Inc.

Formation of Self-Assembled Structures:

The four PNA monomers, either per se, or with one or both protecting groups fluorenylmethyloxycarbonyl (Fmoc) and benzhydryloxycarbonyl (Bhoc), were tested for their ability to self-assemble into ordered structures under a variety of solvents, including organic solvents (methanol, ethanol, dimethyl sulfoxide (DMSO), dimethylformamide (DMF) and hexafluoro-2-isopropanol (HFIP)) and diverse buffer solutions with a range of pH values and concentrations.

Self-assembly of PNA monomers in aqueous solutions was tested by mixing the tested PNA monomer with the aqueous solution to a concentration of up to 5 mg/ml (e.g., 1-5 mg/ml), and heating the mixture at 100° C. under vigorous shaking. The hot solution was optionally filtered, using a 0.22 μm syringe filter (Millipore) into a clean beaker to remove residual undissolved material. Spheres formation, if occurred, was observed in few minutes as the solution is cooled down to room temperature by the rise in turbidity.

The procedure was performed in water, an acidic solution and an alkaline solution. For acidic solutions, HCl was added to the water before heating so as to obtain pH of 2.0.

For alkaline solution, NaOH 1M was added to the water. The PNA monomer was dissolved in the alkaline solution without heating or shaking.

Self assembly of the PNA monomers in organic solvents was similarly tested, but without heating the solution.

Alternatively, a stock solution of the PNA monomer in the organic solvent was prepared (e.g., at a PNA monomer concentration of 50 mg/ml), and was diluted in water at a ratio of e.g., 1:50.

Assembly into spherical species was observed for the double-protected (Fmoc, Bhoc-protected) guanine-based, adenine-based and cytosine-based PNA monomers, and for Fmoc-Thymine in water.

Assembly into spherical species was also observed when a stock solution of these PNA monomers in DMF was prepared and diluted with water at a 1:50 ratio.

FIGS. 1A-C present Dynamic light scattering (DLS) (FIG. 1A), and scanning electron microscopy (SEM) (FIGS. 1B and 1C), of spheres formed of N—(N-Fmoc-2-aminoethyl)-N—[(N-6-Bhoc-9-guanyl)acetyl]-glycine (Fmoc-G-(Bhoc)-aeg-OH) in water, at a concentration of 5 mg/ml.

As shown therein, very uniform spherical assemblies with an average diameter of 1.7 μm were obtained. Such uniformity is very rare in self-assembled biological and other organic systems and the observed spherical species resembled inorganic particles such as silica.

Spheres were observed also for the double-protected PNA monomers of adenine and cytosine, and for Fmoc-thymine in water. These compounds are less soluble in water and the formed spheres were relatively unstable and prone to deformation and precipitation after assembly.

The spheres formed by Fmoc-G-(Bhoc)-aeg-OH remained stable in solution, as well as in the dry state on a solid substrate over time.

No sphere formation was observed under either the alkaline or acidic aqueous solutions, or in organic solvents (without dilution in water).

Example 2

Photonic Structures

Experimental Methods:

Photonic Crystal Formation:

In general, a procedure for forming self-assembled spheres in water is repeated, however, while preparing a solution of at least 5 ml volume (e.g., 5-25 ml or higher volumes). Upon filtration of the hot solution into a beaker, spheres formation is observed in few minutes as the solution is cooled down to room temperature by the rise in turbidity. Formation of photonic crystal is observed shortly after.

In an exemplary procedure, Fmoc-G-(Bhoc)-aeg-OH powder was dissolved in double distilled water to a concentration of 4 mg ml$^{-1}$ by heating the solution to 100° C. and stirring. The hot solution was filtered using a 0.22 μm syringe filter (Millipore) into a clean beaker.

Photonic Crystal Imaging:

A glass substrate was placed in the beaker prior to the filtration of the solution. Following the formation of the photonic crystal, the excess solution was drawn gently using a syringe and needle. The glass was dried in open air.

The obtained photonic crystals were observed under light microscope.

For SEM imaging, the dry glass was coasted with chromium. Images were taken using a JEOL JSM 6700F FE-SEM operating at 10 kV.

Color Tuning:

Following the formation of a photonic crystal, part of the excess solution was drawn gently using a syringe and needle and replaced with sodium chloride solution to a final concentration of up to 75 mg/ml. The color change was captured by video and RGB numbers were obtained using the snapshots presented in FIGS. 3A-B. The RGB numbers were translated to CIE x and y values and placed on the map.

Reflected Light Spectra Measurements:

BLACK-Comet Concave Grating Spectrometer (StellarNet, Inc.) was used to measure the reflected light spectra of deposited films of PNA spheres on glass slides over a black surface at various locations that showed uniform colors. The reflectance was normalized with respect to a white standard of high density Teflon tape.

Results:

As shown in FIG. 2A, when the spheres were prepared in a large volume, the formation of a colorful layer at the interface of the solution and the air was evident. The double-protected PNA monomers firstly self-assemble into spheres in the bulk solution phase. Then, a small fraction of the sphere population at the water-air interface further assembles into a thin layer exhibiting vivid colors.

This layer was deposited onto a solid substrate by gently drawing the solution using a needle, until the layer reaches a substrate that was placed on the bottom a priori, as shown in FIG. 2B.

The extracted solution, which consists of the majority of the spheres population of the original sample, could then be subjected to another cycle of heating and cooling to dissolve and re-assemble the spheres. All of the physical properties observed for the spheres and photonic crystals were similar also after a re-assembly process.

Examination of the deposited colored layer by microscopy revealed a tightly packed monolayer of spheres, as presented in FIGS. 2C-2E.

Although partial disorder due to slight variation in sphere diameter is detected, it is clearly noticeable that the spheres are arranged in a crystalline structure with hexagonal symmetry, as shown in FIGS. 2D and 2E.

These data demonstrate that the self-assembled spheres undergo a secondary self-assembly process to organize into a two-dimensional periodic arrangement. The size of a single crystal is defined by the surface area at the solution/air interface. Thus, larger or smaller crystals can be obtained when wider or narrower vessels are used.

Adult male panther chameleons, a reptilian species found in Madagascar, can rapidly shift their skin color by changing the salt balance in their pigment cells which consist of an array of guanine nanocrystals. The osmotic pressure results in an expansion of the lattice that leads to a shift in reflectivity [Teyssier, et al., Nat. Commun. 2015, 6, 6368].

The effect of the addition of a concentrated salt solution to the PNA photonic crystals was therefore tested, in order to evaluate its effect on the properties of the crystal.

A fresh solution of Fmoc-G-(Bhoc)-aeg-OH in water was prepared, as described above, and photonic crystals of bright purple and yellow were observed. FIG. 3A presents six consecutive snapshots of the same glass vial containing a guanine-based PNA photonic crystal. The interval time between each two successive images was 3 minutes.

Sodium chloride was added to a final concentration of 75 mg/ml by gentle injection of a concentrated salt solution beneath the colored layer. The solution was monitored over time after the addition of the salt and a prompt color change was observed. FIG. 3B presents six consecutive snapshots of the same glass vial after the addition of 75 mg ml$^{-1}$ NaCl, over time. The interval time between each two successive images was 3 minutes. The addition of NaCl took place following the last snapshot shown in FIG. 3A and the change in color was immediate.

FIG. 3C presents the time evolution of the change in color before and after NaCl addition, as presented on the CIE color space. The white arrow indicates the change in color before the addition of NaCl and the black arrow indicates the change after the addition NaCl to the solution. Time evolution of the PNA photonic crystal in the CIE (International Commission on Illumination) color space indicates a gradual spectral transition from the red and yellow to the blue and green portions of the visible electromagnetic spectrum. This experiment was repeated multiple times and color evolution was terminated at different time points by drawing the solution and depositing the colored layers on glass slides.

PNA photonic crystals at different stages of color evolution following the addition of NaCl were deposited on glass slides and the spectra of the reflected light were recorded. The results are presented in FIG. 3D.

Figure 4A:
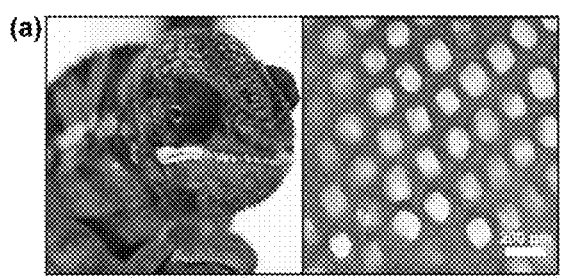
Figure 4B:
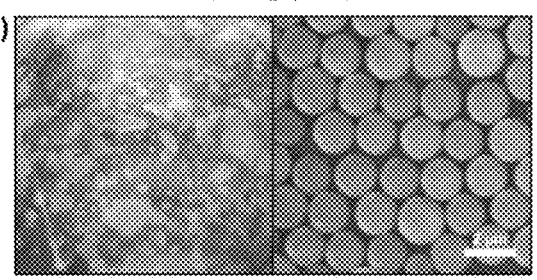

FIGS. 4A and 4B compare the chameleon nano-crystals and the PNA spheres presented herein. Despite the difference in order of magnitude between the sizes of the chameleon nano-crystals and the PNA spheres, both of the guanine-based systems organize in a very similar pattern.

Figure 4C:
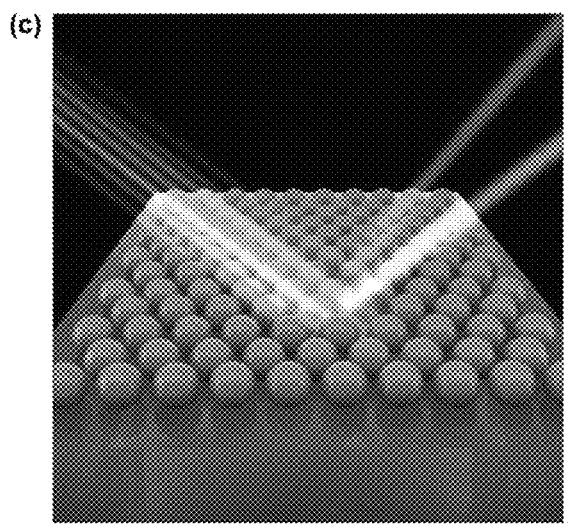
Figure 4D:
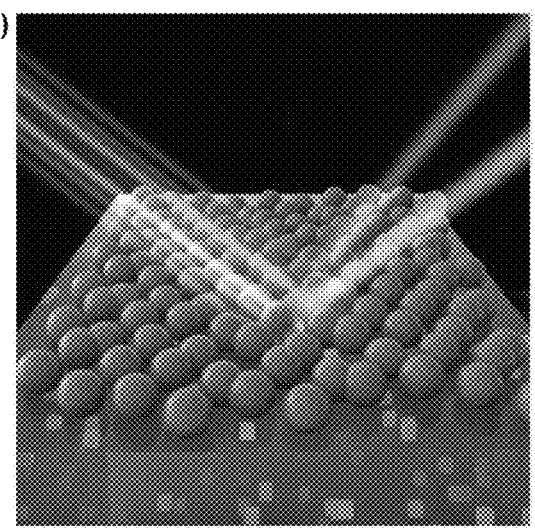

The change in color in the chameleon skin was explained by the alteration of spacing of the guanine crystal lattice between the resting and excited states. Similar change in density is observed following the addition of NaCl to the PNA spheres in solution, as illustrated in FIGS. 4C and 4D. It is known that shifts in geometry of photonic structures can lead to visible changes in the reflected wavelength Arsenault et al., Nat. Photonics 2007, 1, 468].

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An ordered structure composed of a plurality of peptide nucleic acid (PNA) monomers, wherein:

at least a portion of said monomers are N-protected PNA monomers having at least one amine group capped by an N-protecting moiety; and/or at least a portion of said monomers are modified PNA monomers comprising at least one aromatic moiety attached to a backbone, a nucleobase and/or a nucleobase linkage unit of the PNA monomer.

2. The ordered structure of claim 1, wherein each of said PNA monomers is an N-protected monomer.

3. The ordered structure of claim 1, wherein at least a portion of said N-protected PNA monomers have two amine groups each being independently capped by an N-protecting moiety.

4. The ordered structure of claim 1, wherein in at least a portion of said N-protected PNA monomers, said N-protecting moiety is an aromatic N-protecting moiety.

5. The ordered structure of claim 1, wherein each of said N-protected PNA monomers has two amine groups each being independently capped by an aromatic N-protecting moiety.

6. The ordered structure of claim 1, wherein at least a portion of said modified PNA monomers comprise at least two aromatic moieties attached to said backbone, said nucleobase and/or to said linkage unit.

7. The structure of claim 1, wherein at least a portion of said modified PNA monomer comprise at least one aromatic moiety as a substituent of an amine group that forms a part of said backbone or said nucleobase.

8. The structure of claim 6, wherein at least a portion of said modified PNA monomer comprise at least one aromatic moiety as a substituent of an amine group that forms a part of said backbone or said nucleobase.

9. The structure of claim 1, wherein each of said modified PNA monomers is independently represented by Formula I:

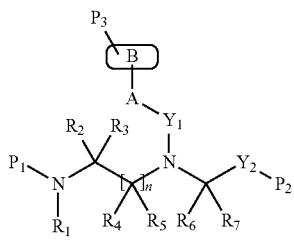

wherein:
B is a nucleobase or an analog thereof;
P₃ is absent, or is said N-protecting group capping an amine group of said nucleobase or an analog thereof, or is said aromatic moiety attached to said nucleobase or an analog thereof;
A is substituted or unsubstituted alkylene or absent;
Y₁ is selected from C=O, C=S, CRaRb, C=NRa, —NRa—, C(=O)O, C(=S)O, C(=S)S, C(=O/S)NRa, NRaC(=O/S), O/S—C(=O/S)NRa, NRaC(=O/S)—O/S, S(=O)₂, S(=O), S(=O/S)NRa, and NRaS(=O/S), with Ra and Rb being each independently selected from hydrogen, alkyl, cycloalkyl, aryl, heteroaryl, and said aromatic moiety, or Y₁ is absent;
n is an integer that ranges from 0 to 4 (being 0, 1, 2, 3 or 4);
R₁-R₇ are each independently selected from hydrogen, alkyl, cycloalkyl, aryl, heteroaryl, hydroxy, alkoxy, thiol, thioalkoxy, aryloxy, thioaryloxy, amine, carboxy, amide, thiocarboxy, carbamate, sulfonyl, sulfate, sulfonamide, and said aromatic moiety, or, alternatively, two or more of R₁-R₇ are joined together to form a cyclic moiety;
Y₂ is C=O, C=S, CRaRb, C=NRa, —NRa—, C(=O)O, C(=S)O, C(=S)S, C(=O/S)NRa, NRaC(=O/S), O/S—C(=O/S)NRa, NRaC(=O/S)—O/S, S(=O)₂, S(=O), S(=O/S)NRa, and NRaS(=O/S), with Ra and Rb being each independently selected from hydrogen, alkyl, aryl, cycloalkyl and said aromatic moiety;
P₂ is selected from hydrogen, alkyl, cycloalkyl, aryl, heteroaryl, and said aromatic moiety, or, alternatively, Y₂ and P₂ form together a carboxylate group capped by a carboxy-protecting moiety or an amine group capped by an N-protecting moiety; and
P₁ is selected from hydrogen, alkyl, cycloalkyl, aryl, heteroaryl or is said N-protecting moiety or is said aromatic moiety,
provided that at least one of P₁, P₂ and P₃ is said N-protecting moiety or is an aromatic moiety.

10. The structure of claim 1, wherein at least a portion of said PNA monomers comprises guanine or a guanine analog as said nucleobase.

11. The structure of claim 1, wherein each of said modified PNA monomers is independently represented by a formula selected from the group consisting of:

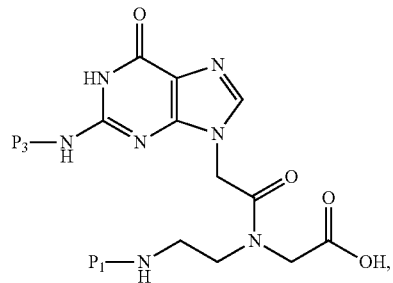

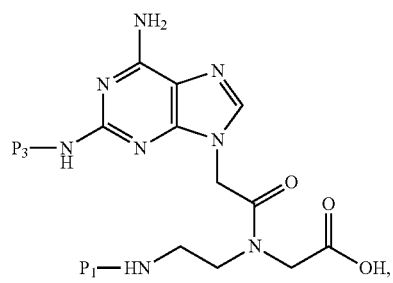

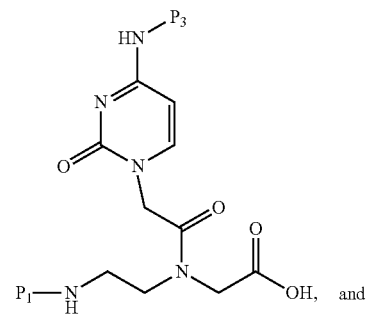

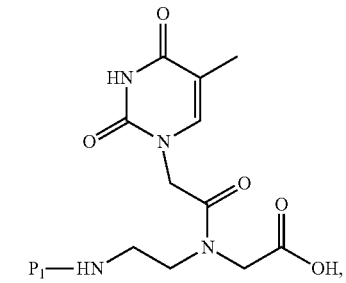

wherein P₁ and P₃, if present, are each independently selected from hydrogen, alkyl, cycloalkyl, aryl, heteroaryl, said N-protecting group and said aromatic group, provided that at least one of P₁ and P₃ is said N-protecting group or said aromatic group.

12. The structure of claim 1, wherein each of said PNA monomers is a modified PNA monomer represented by the Formula:

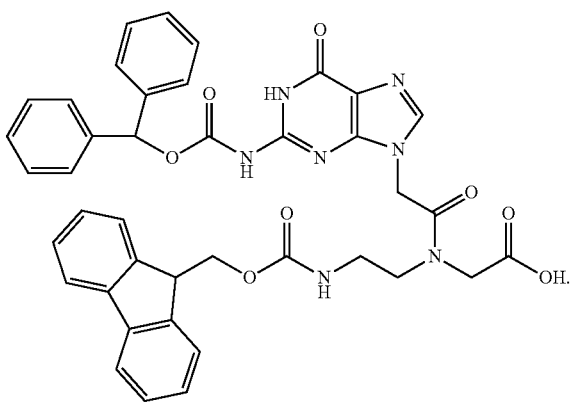 [SMILES: O=C(O)CN(CCNC(=O)OCC1c2ccccc2-c2ccccc21)C(=O)Cn1cnc2c(=O)[nH]c(NC(=O)OC(c3ccccc3)c3ccccc3)nc21]

13. The structure of claim 1, being a substantially spherical structure.

14. A process of preparing an ordered structure composed of a plurality of PNA monomers, the process comprising subjecting a plurality of PNA monomers, at least a portion of which being modified PNA monomers as defined in claim 1, to conditions which favor formation of the ordered structure,
wherein said conditions comprise:
contacting said plurality of PNA monomers with an aqueous solution, to thereby obtain an aqueous solution comprising said plurality of PNA monomers, heating said aqueous solution, and then cooling to room temperature; or,
dissolving said PNA monomers in an organic solvent, so thereby obtain an organic solution comprising said plurality of PNA monomers, and diluting said organic solution with an aqueous solution.

15. An ordered structure prepared by the process of claim 14.

16. A composition comprising a plurality of structures as defined in claim 1.

17. A photonic crystal comprising a plurality of structures as defined in claim 1, said structures being periodically arranged so as to exhibit a periodic modulation in a refractive index thereof.

18. The photonic crystal of claim 17, wherein said structures are arranged to form a two-dimensional ordered array.

19. The photonic crystal of claim 17, characterized by a reflectance wavelength range, wherein said periodic modulation of said refractive index is responsive to an external stimulus and said reflectance wavelength range is shifted in response to said external stimulus.

20. An article-of-manufacturing comprising a matrix and a photonic crystal as defined in claim 17 incorporated in and/or on said matrix.

21. A method of tuning a reflectance wavelength range of a photonic crystal as defined in claim 17, the method comprising changing an osmolarity of an aqueous solution contacting the photonic crystal, said changing comprising adding a water-soluble salt to said aqueous solution to thereby change said osmolarity, thereby tuning the wavelength range of the photonic crystal.

\* \* \* \* \*